(12) United States Patent
Doyle et al.

(10) Patent No.: US 9,993,604 B2
(45) Date of Patent: Jun. 12, 2018

(54) METHODS AND SYSTEMS FOR AN OPTIMIZED PROPORTIONAL ASSIST VENTILATION

(75) Inventors: Peter Doyle, Vista, CA (US); Mehdi M. Jafari, Laguna Hills, CA (US)

(73) Assignee: Covidien LP, Mansfield, MA (US)

( * ) Notice: Subject to any disclaimer, the term of this patent is extended or adjusted under 35 U.S.C. 154(b) by 1199 days.

(21) Appl. No.: 13/457,733

(22) Filed: Apr. 27, 2012

(65) Prior Publication Data
US 2013/0284172 A1   Oct. 31, 2013

(51) Int. Cl.
*A61M 16/00* (2006.01)
*A61M 16/08* (2006.01)

(52) U.S. Cl.
CPC ...... *A61M 16/0051* (2013.01); *A61M 16/026* (2017.08); *A61M 16/0063* (2014.02); *A61M 16/0833* (2014.02); *A61M 2016/0021* (2013.01); *A61M 2016/0027* (2013.01); *A61M 2016/0033* (2013.01); *A61M 2205/502* (2013.01); *A61M 2230/46* (2013.01)

(58) Field of Classification Search
CPC .......... A61M 16/00; A61M 16/0051
See application file for complete search history.

(56) References Cited

U.S. PATENT DOCUMENTS

| | | |
|---|---|---|
| 1,202,125 A | 10/1916 | Tullar |
| 1,202,126 A | 10/1916 | Tullar |
| 1,241,056 A | 9/1917 | Tullar |
| 2,914,067 A | 11/1959 | Meidenbauer |
| 3,339,545 A | 9/1967 | Barnett |
| 3,584,618 A | 6/1971 | Reinhard et al. |
| 3,628,531 A | 12/1971 | Harris |
| 3,643,652 A | 2/1972 | Beltran |
| 3,722,510 A | 3/1973 | Parker |
| 3,739,776 A | 6/1973 | Bird et al. |
| 3,759,249 A | 9/1973 | Fletcher et al. |
| 3,805,780 A | 4/1974 | Cramer et al. |
| 3,911,899 A | 10/1975 | Hattes |
| 3,941,124 A | 3/1976 | Rodewald et al. |
| 3,952,739 A | 4/1976 | Cibulka |
| 3,957,044 A | 5/1976 | Fletcher et al. |
| 3,968,794 A | 7/1976 | O'Neill |
| 3,968,795 A | 7/1976 | O'Neill et al. |

(Continued)

FOREIGN PATENT DOCUMENTS

| | | |
|---|---|---|
| EP | 982043 | 3/2000 |
| EP | 1491227 | 12/2004 |

(Continued)

OTHER PUBLICATIONS

Dong, Feng Dan, "Advanced Control Algorithms for Discrete Linear Repetitive Processes in Self-servowriting of Hard Disk Drives", Disseration, Univ. of California, Berkeley, Spring 2011, 143 pgs.

(Continued)

*Primary Examiner* — Tan-Uyen (Jackie) T Ho
*Assistant Examiner* — Joseph D Boecker

(57) ABSTRACT

This disclosure describes systems and methods for providing an optimized proportional assist breath type during ventilation of a patient. The disclosure describes a novel breath type that delivers a target airway pressure calculated based on a desired patient effort range to a triggering patient.

14 Claims, 4 Drawing Sheets

(56) References Cited

U.S. PATENT DOCUMENTS

| | | |
|---|---|---|
| 3,985,131 A | 10/1976 | Buck et al. |
| 3,991,304 A | 11/1976 | Hillsman |
| 4,056,098 A | 11/1977 | Michel et al. |
| 4,112,931 A * | 9/1978 | Burns .................... 128/205.23 |
| 4,127,123 A | 11/1978 | Bird |
| 4,150,670 A * | 4/1979 | Jewett et al. ............ 128/204.22 |
| 4,258,718 A | 3/1981 | Goldman |
| 4,281,651 A | 8/1981 | Cox |
| 4,284,075 A | 8/1981 | Krasberg |
| 4,294,242 A | 10/1981 | Cowans |
| 4,299,236 A | 11/1981 | Poirier |
| 4,305,388 A | 12/1981 | Brisson |
| 4,316,182 A | 2/1982 | Hodgson |
| 4,340,044 A | 7/1982 | Levy et al. |
| 4,366,821 A | 1/1983 | Wittmaier et al. |
| 4,433,693 A | 2/1984 | Hochstein |
| 4,440,166 A | 4/1984 | Winkler et al. |
| 4,442,835 A | 4/1984 | Carnegie |
| 4,448,192 A | 5/1984 | Stawitcke et al. |
| 4,459,982 A | 7/1984 | Fry |
| 4,498,471 A | 2/1985 | Kranz et al. |
| 4,503,850 A | 3/1985 | Pasternak |
| 4,506,667 A | 3/1985 | Ansite |
| 4,522,639 A | 6/1985 | Ansite et al. |
| 4,527,557 A | 7/1985 | DeVries et al. |
| 4,550,726 A | 11/1985 | McEwen |
| 4,606,340 A | 8/1986 | Ansite |
| 4,630,605 A | 12/1986 | Pasternack |
| 4,637,385 A | 1/1987 | Rusz |
| 4,648,407 A | 3/1987 | Sackner |
| 4,653,493 A | 3/1987 | Hoppough |
| 4,655,213 A | 4/1987 | Rapoport et al. |
| 4,752,089 A | 6/1988 | Carter |
| 4,773,411 A | 9/1988 | Downs |
| 4,805,612 A | 2/1989 | Jensen |
| 4,805,613 A | 2/1989 | Bird |
| 4,821,709 A | 4/1989 | Jensen |
| 4,870,960 A | 10/1989 | Hradek |
| 4,921,642 A | 5/1990 | LaTorraca |
| 4,939,647 A | 7/1990 | Clough et al. |
| 4,954,799 A | 9/1990 | Kumar |
| 4,971,052 A | 11/1990 | Edwards |
| 4,984,158 A | 1/1991 | Hillsman |
| 4,986,268 A | 1/1991 | Tehrani |
| 4,990,894 A | 2/1991 | Loescher et al. |
| 5,022,393 A | 6/1991 | McGrady et al. |
| 5,044,362 A | 9/1991 | Younes |
| 5,048,515 A | 9/1991 | Sanso |
| 5,057,822 A | 10/1991 | Hoffman |
| 5,072,737 A | 12/1991 | Goulding |
| 5,094,235 A | 3/1992 | Westenskow et al. |
| 5,107,830 A | 4/1992 | Younes |
| 5,107,831 A | 4/1992 | Halpern et al. |
| 5,148,802 A | 9/1992 | Sanders et al. |
| 5,150,291 A | 9/1992 | Cummings et al. |
| 5,156,145 A | 10/1992 | Flood et al. |
| 5,161,525 A | 11/1992 | Kimm et al. |
| 5,165,397 A | 11/1992 | Arp |
| 5,165,398 A | 11/1992 | Bird |
| 5,237,987 A | 8/1993 | Anderson et al. |
| 5,239,995 A | 8/1993 | Estes et al. |
| 5,271,389 A | 12/1993 | Isaza et al. |
| 5,273,031 A | 12/1993 | Olsson et al. |
| 5,279,549 A | 1/1994 | Ranford |
| 5,299,568 A | 4/1994 | Forare et al. |
| 5,301,921 A | 4/1994 | Kumar |
| 5,307,795 A | 5/1994 | Whitwam et al. |
| 5,313,937 A | 5/1994 | Zdrojkowski |
| 5,315,989 A | 5/1994 | Tobia |
| 5,316,009 A | 5/1994 | Yamada |
| 5,319,540 A | 6/1994 | Isaza et al. |
| 5,322,059 A | 6/1994 | Walther |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,353,788 A | 10/1994 | Miles |
| 5,357,946 A | 10/1994 | Kee et al. |
| 5,365,922 A | 11/1994 | Raemer |
| 5,368,019 A | 11/1994 | LaTorraca |
| 5,383,449 A | 1/1995 | Forare et al. |
| 5,385,142 A | 1/1995 | Brady et al. |
| 5,388,575 A | 2/1995 | Taube |
| 5,390,666 A | 2/1995 | Kimm et al. |
| 5,398,676 A | 3/1995 | Press et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,433,193 A | 7/1995 | Sanders et al. |
| 5,438,980 A | 8/1995 | Phillips |
| 5,443,075 A | 8/1995 | Holscher |
| 5,452,714 A | 9/1995 | Anderson et al. |
| 5,477,860 A | 12/1995 | Essen Moller |
| 5,485,833 A | 1/1996 | Dietz |
| 5,492,113 A | 2/1996 | Estes et al. |
| 5,503,147 A | 4/1996 | Bertheau |
| 5,507,282 A | 4/1996 | Younes |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,524,616 A | 6/1996 | Smith et al. |
| RE35,295 E | 7/1996 | Estes et al. |
| 5,531,221 A | 7/1996 | Power |
| 5,535,738 A | 7/1996 | Estes et al. |
| 5,540,218 A | 7/1996 | Jones et al. |
| 5,540,220 A | 7/1996 | Gropper et al. |
| 5,540,222 A | 7/1996 | Younes |
| 5,542,415 A | 8/1996 | Brady |
| 5,544,674 A | 8/1996 | Kelly |
| 5,549,106 A | 8/1996 | Gruenke et al. |
| 5,551,418 A | 9/1996 | Estes et al. |
| 5,551,419 A | 9/1996 | Froehlich et al. |
| 5,572,993 A | 11/1996 | Kurome et al. |
| 5,582,163 A | 12/1996 | Bonassa |
| 5,582,182 A | 12/1996 | Hillsman |
| 5,596,984 A | 1/1997 | O'Mahoney et al. |
| 5,598,838 A | 2/1997 | Servidio et al. |
| 5,605,151 A | 2/1997 | Lynn |
| 5,608,647 A | 3/1997 | Rubsamen et al. |
| 5,623,923 A | 4/1997 | Bertheau et al. |
| 5,630,411 A | 5/1997 | Holscher |
| 5,632,269 A | 5/1997 | Zdrojkowski |
| 5,632,270 A | 5/1997 | O'Mahoney et al. |
| 5,645,048 A | 7/1997 | Brodsky et al. |
| 5,660,171 A | 8/1997 | Kimm et al. |
| 5,662,099 A | 9/1997 | Tobia et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,685,318 A | 11/1997 | Elghazzawi |
| 5,692,497 A | 12/1997 | Schnitzer et al. |
| 5,694,923 A | 12/1997 | Hete et al. |
| 5,704,345 A | 1/1998 | Berthon-Jones |
| 5,715,812 A | 2/1998 | Deighan et al. |
| 5,720,278 A * | 2/1998 | Lachmann ............ A61M 16/00 128/204.21 |
| 5,730,121 A | 3/1998 | Hawkins, Jr. et al. |
| 5,735,267 A | 4/1998 | Tobia |
| 5,743,253 A | 4/1998 | Castor et al. |
| 5,752,506 A | 5/1998 | Richardson |
| 5,752,509 A | 5/1998 | Lachmann et al. |
| 5,762,480 A | 6/1998 | Adahan |
| 5,765,558 A | 6/1998 | Psaros et al. |
| 5,771,884 A | 6/1998 | Yarnall et al. |
| 5,782,233 A | 7/1998 | Niemi et al. |
| 5,791,339 A | 8/1998 | Winter |
| 5,794,615 A | 8/1998 | Estes |

(56) References Cited

U.S. PATENT DOCUMENTS

| | | |
|---|---|---|
| 5,794,986 A | 8/1998 | Gansel et al. |
| 5,803,065 A | 9/1998 | Zdrojkowski et al. |
| 5,810,741 A | 9/1998 | Essen Moller |
| 5,813,399 A | 9/1998 | Isaza et al. |
| 5,823,187 A | 10/1998 | Estes et al. |
| 5,826,575 A | 10/1998 | Lall |
| 5,829,441 A | 11/1998 | Kidd et al. |
| 5,832,916 A | 11/1998 | Lundberg |
| 5,832,919 A | 11/1998 | Kano et al. |
| 5,860,418 A | 1/1999 | Lundberg |
| 5,864,938 A | 2/1999 | Gansel et al. |
| 5,865,168 A | 2/1999 | Isaza |
| 5,868,133 A | 2/1999 | DeVries et al. |
| 5,876,353 A | 3/1999 | Riff |
| 5,878,744 A | 3/1999 | Pfeiffer |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,891,023 A | 4/1999 | Lynn |
| 5,901,704 A | 5/1999 | Estes et al. |
| 5,904,141 A | 5/1999 | Estes et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,931,160 A | 8/1999 | Gilmore et al. |
| 5,934,274 A | 8/1999 | Merrick et al. |
| 5,937,853 A * | 8/1999 | Strom .................. A61M 16/00 128/204.18 |
| 5,957,130 A | 9/1999 | Krahbichler et al. |
| 5,964,218 A | 10/1999 | Smith et al. |
| 5,970,975 A | 10/1999 | Estes et al. |
| 5,975,081 A | 11/1999 | Hood et al. |
| 5,996,580 A | 12/1999 | Swann |
| 6,024,089 A | 2/2000 | Wallace et al. |
| 6,029,660 A | 2/2000 | Calluaud et al. |
| 6,029,664 A | 2/2000 | Zdrojkowski et al. |
| 6,029,665 A | 2/2000 | Berthon-Jones |
| 6,041,777 A | 3/2000 | Faithfull et al. |
| 6,041,780 A | 3/2000 | Richard et al. |
| 6,047,860 A | 4/2000 | Sanders |
| 6,076,523 A | 6/2000 | Jones et al. |
| 6,105,575 A | 8/2000 | Estes et al. |
| 6,109,259 A | 8/2000 | Fitzgerald |
| 6,112,744 A | 9/2000 | Hognelid |
| 6,116,240 A | 9/2000 | Merrick et al. |
| 6,116,464 A | 9/2000 | Sanders |
| 6,123,073 A | 9/2000 | Schlawin et al. |
| 6,123,074 A | 9/2000 | Hete et al. |
| 6,135,105 A | 10/2000 | Lampotang et al. |
| 6,135,106 A | 10/2000 | Dirks et al. |
| 6,139,506 A | 10/2000 | Heinonen |
| 6,142,150 A | 11/2000 | O'Mahony et al. |
| 6,148,814 A | 11/2000 | Clemmer et al. |
| 6,158,432 A | 12/2000 | Biondi et al. |
| 6,161,539 A | 12/2000 | Winter |
| 6,168,568 B1 | 1/2001 | Gavriely |
| 6,196,222 B1 | 3/2001 | Heinonen et al. |
| 6,209,540 B1 | 4/2001 | Sugiura et al. |
| 6,213,119 B1 | 4/2001 | Brydon et al. |
| 6,213,120 B1 | 4/2001 | Block et al. |
| 6,216,690 B1 | 4/2001 | Keitel et al. |
| 6,220,245 B1 | 4/2001 | Takabayashi et al. |
| 6,223,064 B1 | 4/2001 | Lynn et al. |
| 6,227,197 B1 | 5/2001 | Fitzgerald |
| 6,240,919 B1 | 6/2001 | MacDonald et al. |
| 6,253,765 B1 | 7/2001 | Hognelid et al. |
| 6,257,234 B1 | 7/2001 | Sun |
| 6,258,039 B1 | 7/2001 | Okamoto et al. |
| 6,269,812 B1 | 8/2001 | Wallace et al. |
| 6,273,088 B1 | 8/2001 | Hillsman |
| 6,273,444 B1 | 8/2001 | Power |
| 6,283,119 B1 | 9/2001 | Bourdon |
| 6,302,105 B1 | 10/2001 | Wickham et al. |
| 6,302,851 B1 | 10/2001 | Gedeon |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,321,748 B1 | 11/2001 | O'Mahoney |
| 6,325,785 B1 | 12/2001 | Babkes et al. |
| 6,341,604 B1 | 1/2002 | Kellon |
| 6,342,039 B1 | 1/2002 | Lynn et al. |
| 6,345,619 B1 | 2/2002 | Finn |
| 6,357,438 B1 | 3/2002 | Hansen |
| 6,360,745 B1 | 3/2002 | Wallace et al. |
| 6,369,838 B1 | 4/2002 | Wallace et al. |
| 6,371,113 B1 | 4/2002 | Tobia et al. |
| 6,371,114 B1 | 4/2002 | Schmidt et al. |
| 6,390,091 B1 * | 5/2002 | Banner .............. A61M 16/0051 128/202.22 |
| 6,397,838 B1 | 6/2002 | Zimlich, Jr. et al. |
| 6,412,483 B1 | 7/2002 | Jones et al. |
| 6,427,689 B1 | 8/2002 | Estes et al. |
| 6,431,169 B1 | 8/2002 | do Val et al. |
| 6,439,229 B1 | 8/2002 | Du et al. |
| 6,446,630 B1 | 9/2002 | Todd, Jr. |
| 6,457,472 B1 | 10/2002 | Schwartz et al. |
| 6,467,477 B1 | 10/2002 | Frank et al. |
| 6,467,478 B1 | 10/2002 | Merrick et al. |
| 6,467,481 B1 | 10/2002 | Eswarappa |
| 6,484,719 B1 | 11/2002 | Berthon-Jones |
| 6,512,938 B2 | 1/2003 | Claure et al. |
| 6,526,970 B2 | 3/2003 | DeVries et al. |
| 6,532,956 B2 | 3/2003 | Hill |
| 6,532,957 B2 | 3/2003 | Berthon-Jones |
| 6,532,958 B1 | 3/2003 | Buan et al. |
| 6,532,959 B1 | 3/2003 | Berthon-Jones |
| 6,532,960 B1 | 3/2003 | Yurko |
| 6,536,429 B1 | 3/2003 | Pavlov et al. |
| 6,536,433 B1 | 3/2003 | Cewers |
| 6,539,940 B2 | 4/2003 | Zdrojkowski et al. |
| 6,543,449 B1 | 4/2003 | Woodring et al. |
| 6,546,930 B1 | 4/2003 | Emerson et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,561,187 B2 | 5/2003 | Schmidt et al. |
| 6,571,795 B2 | 6/2003 | Bourdon |
| 6,575,163 B1 | 6/2003 | Berthon-Jones |
| 6,577,884 B1 | 6/2003 | Boas |
| 6,578,575 B1 | 6/2003 | Jonson |
| 6,581,597 B2 | 6/2003 | Sugiura |
| 6,588,422 B1 | 7/2003 | Berthon-Jones et al. |
| 6,595,213 B2 | 7/2003 | Bennarsten |
| 6,607,481 B1 | 8/2003 | Clawson |
| 6,609,016 B1 | 8/2003 | Lynn |
| 6,609,517 B1 | 8/2003 | Estes et al. |
| 6,612,995 B2 | 9/2003 | Leonhardt et al. |
| 6,622,726 B1 | 9/2003 | Du |
| 6,626,175 B2 | 9/2003 | Jafari et al. |
| 6,629,527 B1 | 10/2003 | Estes et al. |
| 6,629,934 B2 | 10/2003 | Mault et al. |
| 6,631,716 B1 | 10/2003 | Robinson et al. |
| 6,640,806 B2 | 11/2003 | Yurko |
| 6,644,310 B1 | 11/2003 | Delache et al. |
| 6,644,312 B2 | 11/2003 | Berthon-Jones et al. |
| 6,651,657 B1 | 11/2003 | Manigel et al. |
| 6,655,383 B1 | 12/2003 | Lundberg |
| 6,668,824 B1 | 12/2003 | Isaza et al. |
| 6,671,529 B2 | 12/2003 | Claure et al. |
| 6,672,300 B1 | 1/2004 | Grant |
| 6,675,797 B1 | 1/2004 | Berthon-Jones |
| 6,675,801 B2 | 1/2004 | Wallace et al. |
| 6,679,258 B1 | 1/2004 | Strom |
| 6,688,307 B2 | 2/2004 | Berthon-Jones |
| 6,708,691 B1 | 3/2004 | Hayek |
| 6,718,974 B1 | 4/2004 | Moberg |
| 6,723,055 B2 | 4/2004 | Hoffman |
| 6,725,447 B1 | 4/2004 | Gilman et al. |

(56) References Cited

U.S. PATENT DOCUMENTS

| | | |
|---|---|---|
| 6,739,337 B2 | 5/2004 | Isaza |
| 6,748,252 B2 | 6/2004 | Lynn et al. |
| 6,752,151 B2 | 6/2004 | Hill |
| 6,755,193 B2 | 6/2004 | Berthon-Jones et al. |
| 6,758,216 B1 * | 7/2004 | Berthon-Jones .... A61M 16/026 128/204.18 |
| 6,758,217 B1 | 7/2004 | Younes |
| 6,760,608 B2 | 7/2004 | Lynn |
| 6,761,165 B2 | 7/2004 | Strickland, Jr. |
| 6,761,167 B1 | 7/2004 | Nadjafizadeh et al. |
| 6,761,168 B1 | 7/2004 | Nadjafizadeh et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,820,613 B2 | 11/2004 | Wankebach et al. |
| 6,820,618 B2 | 11/2004 | Banner et al. |
| 6,823,866 B2 | 11/2004 | Jafari et al. |
| 6,837,241 B2 | 1/2005 | Samzelius |
| 6,837,242 B2 | 1/2005 | Younes |
| 6,837,244 B2 | 1/2005 | Yagi et al. |
| 6,854,462 B2 | 2/2005 | Berthon-Jones et al. |
| 6,860,858 B2 | 3/2005 | Green et al. |
| 6,866,040 B1 | 3/2005 | Bourdon |
| 6,868,346 B2 | 3/2005 | Larson et al. |
| 6,877,511 B2 | 4/2005 | DeVries et al. |
| 6,899,101 B2 | 5/2005 | Haston et al. |
| 6,899,103 B1 | 5/2005 | Hood et al. |
| 6,910,480 B1 | 6/2005 | Berthon-Jones |
| 6,915,803 B2 | 7/2005 | Berthon-Jones et al. |
| 6,920,878 B2 | 7/2005 | Sinderby et al. |
| 6,932,084 B2 | 8/2005 | Estes et al. |
| 6,948,497 B2 | 9/2005 | Zdrojkowski et al. |
| 6,949,133 B2 | 9/2005 | McCombs et al. |
| 6,960,854 B2 | 11/2005 | Nadjafizadeh et al. |
| 6,976,487 B1 | 12/2005 | Melker et al. |
| 6,990,977 B1 | 1/2006 | Calluaud et al. |
| 6,997,881 B2 | 2/2006 | Green et al. |
| 7,000,610 B2 | 2/2006 | Bennarsten et al. |
| 7,000,612 B2 | 2/2006 | Jafari et al. |
| 7,008,380 B1 | 3/2006 | Rees et al. |
| 7,013,892 B2 | 3/2006 | Estes et al. |
| 7,021,310 B1 | 4/2006 | Sinderby et al. |
| 7,032,589 B2 | 4/2006 | Kerechanin, II et al. |
| 7,036,504 B2 | 5/2006 | Wallace et al. |
| 7,040,320 B2 | 5/2006 | Fjeld et al. |
| 7,040,321 B2 | 5/2006 | Göbel |
| 7,055,522 B2 | 6/2006 | Berthon-Jones |
| 7,066,173 B2 | 6/2006 | Banner et al. |
| 7,077,131 B2 | 7/2006 | Hansen |
| 7,081,095 B2 | 7/2006 | Lynn et al. |
| RE39,225 E | 8/2006 | Isaza et al. |
| 7,089,930 B2 | 8/2006 | Adams et al. |
| 7,089,936 B2 | 8/2006 | Madaus et al. |
| 7,089,937 B2 | 8/2006 | Berthon-Jones et al. |
| 7,092,757 B2 | 8/2006 | Larson et al. |
| 7,096,866 B2 | 8/2006 | Be'eri et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,137,389 B2 | 11/2006 | Berthon-Jones |
| 7,152,598 B2 | 12/2006 | Morris et al. |
| 7,162,296 B2 | 1/2007 | Leonhardt et al. |
| 7,210,478 B2 | 5/2007 | Banner et al. |
| 7,225,013 B2 | 5/2007 | Geva et al. |
| 7,229,430 B2 | 6/2007 | Hickle et al. |
| 7,246,618 B2 | 7/2007 | Habashi |
| 7,255,103 B2 | 8/2007 | Bassin |
| 7,267,121 B2 | 9/2007 | Ivri |
| 7,267,122 B2 | 9/2007 | Hill |
| 7,270,126 B2 | 9/2007 | Wallace et al. |
| 7,270,128 B2 | 9/2007 | Berthon-Jones et al. |
| 7,275,540 B2 | 10/2007 | Bolam et al. |
| 7,296,573 B2 | 11/2007 | Estes et al. |
| 7,297,119 B2 | 11/2007 | Westbrook et al. |
| 7,305,987 B2 | 12/2007 | Schöller et al. |
| 7,320,320 B2 | 1/2008 | Berthon-Jones |
| 7,331,343 B2 | 2/2008 | Schmidt et al. |
| 7,334,578 B2 | 2/2008 | Biondi et al. |
| 7,347,204 B1 | 3/2008 | Lindsey et al. |
| 7,353,824 B1 | 4/2008 | Forsyth et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| RE40,402 E | 6/2008 | Leonhardt et al. |
| 7,398,115 B2 | 7/2008 | Lynn |
| 7,406,870 B2 | 8/2008 | Seto |
| 7,428,902 B2 | 9/2008 | Du et al. |
| 7,448,381 B2 | 11/2008 | Sasaki et al. |
| 7,455,583 B2 | 11/2008 | Taya |
| 7,455,717 B2 | 11/2008 | Sprinkle |
| 7,460,959 B2 | 12/2008 | Jafari |
| 7,472,702 B2 | 1/2009 | Beck et al. |
| 7,475,685 B2 | 1/2009 | Dietz et al. |
| 7,484,508 B2 | 2/2009 | Younes |
| 7,487,773 B2 | 2/2009 | Li |
| 7,495,546 B2 | 2/2009 | Lintell et al. |
| 7,509,957 B2 | 3/2009 | Duquette et al. |
| 7,516,742 B2 | 4/2009 | Stenzler et al. |
| 7,520,279 B2 | 4/2009 | Berthon-Jones |
| 7,527,054 B2 | 5/2009 | Misholi |
| 7,533,670 B1 | 5/2009 | Freitag et al. |
| 7,556,038 B2 | 7/2009 | Kirby et al. |
| 7,588,031 B2 | 9/2009 | Truschel et al. |
| 7,591,830 B2 | 9/2009 | Rutter |
| 7,610,914 B2 | 11/2009 | Bolam et al. |
| 7,617,824 B2 | 11/2009 | Doyle |
| 7,621,270 B2 | 11/2009 | Morris et al. |
| 7,621,271 B2 | 11/2009 | Brugnoli |
| 7,644,713 B2 | 1/2010 | Berthon-Jones |
| 7,654,802 B2 | 2/2010 | Crawford, Jr. et al. |
| 7,668,579 B2 | 2/2010 | Lynn |
| 7,672,720 B2 | 3/2010 | Heath |
| 7,678,058 B2 | 3/2010 | Patangay et al. |
| 7,678,061 B2 | 3/2010 | Lee et al. |
| 7,682,312 B2 | 3/2010 | Lurie |
| 7,690,378 B1 | 4/2010 | Turcott |
| 7,694,677 B2 | 4/2010 | Tang |
| 7,697,990 B2 | 4/2010 | Ujhazy et al. |
| 7,708,016 B2 | 5/2010 | Zaiser et al. |
| 7,717,110 B2 | 5/2010 | Kane et al. |
| 7,717,111 B2 | 5/2010 | Schneider et al. |
| 7,717,113 B2 | 5/2010 | Andrieux |
| 7,722,546 B2 | 5/2010 | Madaus et al. |
| D618,356 S | 6/2010 | Ross |
| 7,727,160 B2 | 6/2010 | Green et al. |
| 7,730,886 B2 | 6/2010 | Berthon-Jones |
| 7,751,894 B1 | 7/2010 | Freeberg |
| 7,758,503 B2 | 7/2010 | Lynn et al. |
| 7,763,097 B2 | 7/2010 | Federspiel et al. |
| 7,770,578 B2 | 8/2010 | Estes et al. |
| 7,779,834 B2 | 8/2010 | Calluaud et al. |
| 7,784,461 B2 | 8/2010 | Figueiredo et al. |
| 7,793,659 B2 | 9/2010 | Breen |
| 7,802,571 B2 | 9/2010 | Tehrani |
| 7,810,496 B2 | 10/2010 | Estes et al. |
| 7,810,497 B2 | 10/2010 | Pittman et al. |
| 7,819,815 B2 | 10/2010 | Younes |
| 7,823,588 B2 | 11/2010 | Hansen |
| 7,849,854 B2 | 12/2010 | DeVries et al. |
| 7,855,716 B2 | 12/2010 | McCreary et al. |
| 7,866,318 B2 | 1/2011 | Bassin |
| 7,874,293 B2 | 1/2011 | Gunaratnam et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| 7,914,459 B2 | 3/2011 | Green et al. |
| D638,852 S | 5/2011 | Skidmore et al. |
| 7,934,499 B2 | 5/2011 | Berthon-Jones |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,002,711 B2 | 8/2011 | Wood et al. |

(56) References Cited

U.S. PATENT DOCUMENTS

| | | |
|---|---|---|
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| D692,556 S | 10/2013 | Winter |
| D693,001 S | 11/2013 | Winter |
| D701,601 S | 3/2014 | Winter |
| 8,792,949 B2 | 7/2014 | Baker, Jr. |
| 2001/0004893 A1* | 6/2001 | Biondi .............. A61M 16/00 128/204.18 |
| 2001/0035186 A1 | 11/2001 | Hill |
| 2002/0153006 A1 | 10/2002 | Zimlich et al. |
| 2002/0153009 A1 | 10/2002 | Chornyj et al. |
| 2002/0185126 A1 | 12/2002 | Krebs |
| 2003/0010339 A1* | 1/2003 | Banner ............ A61M 16/026 128/204.18 |
| 2003/0121519 A1* | 7/2003 | Estes ................ A61M 16/0051 128/204.18 |
| 2003/0176804 A1 | 9/2003 | Melker |
| 2004/0003814 A1 | 1/2004 | Banner et al. |
| 2004/0050387 A1 | 3/2004 | Younes |
| 2004/0149282 A1 | 8/2004 | Hickle |
| 2005/0039748 A1 | 2/2005 | Andrieux |
| 2005/0121035 A1 | 6/2005 | Martin |
| 2005/0139212 A1 | 6/2005 | Bourdon |
| 2005/0172965 A1 | 8/2005 | Thulin |
| 2006/0009708 A1 | 1/2006 | Rapoport et al. |
| 2006/0060198 A1 | 3/2006 | Aylsworth et al. |
| 2006/0112959 A1 | 6/2006 | Mechlenburg et al. |
| 2006/0142815 A1 | 6/2006 | Tehrani et al. |
| 2006/0144397 A1 | 7/2006 | Wallace et al. |
| 2006/0155206 A1 | 7/2006 | Lynn |
| 2006/0155207 A1 | 7/2006 | Lynn et al. |
| 2006/0155336 A1 | 7/2006 | Heath |
| 2006/0161071 A1 | 7/2006 | Lynn et al. |
| 2006/0174884 A1 | 8/2006 | Habashi |
| 2006/0178591 A1 | 8/2006 | Hempfling |
| 2006/0189880 A1 | 8/2006 | Lynn et al. |
| 2006/0195041 A1 | 8/2006 | Lynn et al. |
| 2006/0235324 A1 | 10/2006 | Lynn |
| 2006/0241708 A1 | 10/2006 | Boute |
| 2006/0243275 A1 | 11/2006 | Ruckdeschel et al. |
| 2006/0249148 A1 | 11/2006 | Younes |
| 2006/0264762 A1 | 11/2006 | Starr |
| 2006/0272642 A1 | 12/2006 | Chalvignac |
| 2006/0278223 A1 | 12/2006 | Younes |
| 2007/0000494 A1* | 1/2007 | Banner ............ A61B 5/0205 128/204.23 |
| 2007/0017510 A1 | 1/2007 | Riedo |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0044796 A1 | 3/2007 | Zdrojkowski et al. |
| 2007/0044799 A1 | 3/2007 | Hete et al. |
| 2007/0044805 A1 | 3/2007 | Wedler et al. |
| 2007/0066961 A1 | 3/2007 | Rutter |
| 2007/0072541 A1 | 3/2007 | Daniels, II et al. |
| 2007/0077200 A1 | 4/2007 | Baker |
| 2007/0093721 A1 | 4/2007 | Lynn et al. |
| 2007/0129647 A1 | 6/2007 | Lynn |
| 2007/0149860 A1 | 6/2007 | Lynn et al. |
| 2007/0151563 A1 | 7/2007 | Ozaki |
| 2007/0157931 A1 | 7/2007 | Parker et al. |
| 2007/0163579 A1 | 7/2007 | Li et al. |
| 2007/0167853 A1 | 7/2007 | Melker et al. |
| 2007/0191697 A1 | 8/2007 | Lynn et al. |
| 2007/0203448 A1 | 8/2007 | Melker et al. |
| 2007/0215146 A1 | 9/2007 | Douglas et al. |
| 2007/0215154 A1 | 9/2007 | Borrello |
| 2007/0227537 A1 | 10/2007 | Bemister et al. |
| 2007/0232951 A1 | 10/2007 | Euliano et al. |
| 2007/0272241 A1 | 11/2007 | Sanborn et al. |
| 2007/0272242 A1 | 11/2007 | Sanborn et al. |
| 2007/0277823 A1 | 12/2007 | Al-Ali et al. |
| 2007/0284361 A1 | 12/2007 | Nadjafizadeh et al. |
| 2008/0000479 A1 | 1/2008 | Elaz et al. |
| 2008/0011301 A1 | 1/2008 | Qian |
| 2008/0017189 A1 | 1/2008 | Ruckdeschel et al. |
| 2008/0017198 A1 | 1/2008 | Ivri |
| 2008/0029097 A1 | 2/2008 | Schatzl |
| 2008/0035145 A1 | 2/2008 | Adams et al. |
| 2008/0045813 A1 | 2/2008 | Phuah et al. |
| 2008/0053441 A1* | 3/2008 | Gottlib et al. ............ 128/204.23 |
| 2008/0053443 A1 | 3/2008 | Estes et al. |
| 2008/0053444 A1 | 3/2008 | Estes et al. |
| 2008/0066752 A1 | 3/2008 | Baker et al. |
| 2008/0066753 A1 | 3/2008 | Martin et al. |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0077033 A1* | 3/2008 | Figueiredo et al. .......... 600/529 |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0110461 A1 | 5/2008 | Mulqueeny et al. |
| 2008/0110462 A1 | 5/2008 | Chekal et al. |
| 2008/0142012 A1 | 6/2008 | Farnsworth et al. |
| 2008/0163872 A1 | 7/2008 | Negele et al. |
| 2008/0178880 A1 | 7/2008 | Christopher et al. |
| 2008/0178882 A1 | 7/2008 | Christopher et al. |
| 2008/0183095 A1 | 7/2008 | Austin et al. |
| 2008/0185002 A1 | 8/2008 | Berthon-Jones et al. |
| 2008/0196720 A1 | 8/2008 | Kollmeyer et al. |
| 2008/0200775 A1 | 8/2008 | Lynn |
| 2008/0200819 A1 | 8/2008 | Lynn et al. |
| 2008/0202528 A1 | 8/2008 | Carter et al. |
| 2008/0216832 A1 | 9/2008 | Carter et al. |
| 2008/0216833 A1 | 9/2008 | Pujol et al. |
| 2008/0230065 A1 | 9/2008 | Heinonen |
| 2008/0234595 A1 | 9/2008 | Ranieri et al. |
| 2008/0236582 A1* | 10/2008 | Tehrani .................. A61H 31/02 128/204.22 |
| 2008/0251079 A1 | 10/2008 | Richey |
| 2008/0257349 A1 | 10/2008 | Hedner et al. |
| 2008/0276939 A1 | 11/2008 | Tiedje |
| 2008/0283061 A1 | 11/2008 | Tiedje |
| 2008/0295839 A1 | 12/2008 | Habashi |
| 2008/0308105 A1 | 12/2008 | Alder et al. |
| 2008/0314385 A1 | 12/2008 | Brunner et al. |
| 2009/0020120 A1 | 1/2009 | Schatzl et al. |
| 2009/0038616 A1 | 2/2009 | Mulcahy et al. |
| 2009/0056719 A1 | 3/2009 | Newman, Jr. |
| 2009/0078258 A1 | 3/2009 | Bowman et al. |
| 2009/0084381 A1 | 4/2009 | DeVries et al. |
| 2009/0095298 A1 | 4/2009 | Gunaratnam et al. |
| 2009/0107502 A1 | 4/2009 | Younes |
| 2009/0114224 A1 | 5/2009 | Handzsuj et al. |
| 2009/0139522 A1 | 6/2009 | Thomson et al. |
| 2009/0159082 A1 | 6/2009 | Eger |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0173347 A1 | 7/2009 | Berthon-Jones |
| 2009/0188502 A1 | 7/2009 | Tiedje |
| 2009/0199855 A1 | 8/2009 | Davenport |
| 2009/0205661 A1 | 8/2009 | Stephenson et al. |

(56) References Cited

U.S. PATENT DOCUMENTS

| | | |
|---|---|---|
| 2009/0205663 A1 | 8/2009 | Vandine et al. |
| 2009/0221926 A1 | 9/2009 | Younes |
| 2009/0229611 A1 | 9/2009 | Martin et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0259135 A1 | 10/2009 | Stasz |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0308394 A1 | 12/2009 | Levi |
| 2010/0006098 A1 | 1/2010 | McGinnis et al. |
| 2010/0008466 A1 | 1/2010 | Balakin |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065055 A1 | 3/2010 | Morris et al. |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078019 A1 | 4/2010 | Rittner et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0083968 A1 | 4/2010 | Wondka et al. |
| 2010/0137380 A1 | 6/2010 | Maybaum |
| 2010/0137723 A1 | 6/2010 | Patangay et al. |
| 2010/0137729 A1 | 6/2010 | Pierry et al. |
| 2010/0137730 A1 | 6/2010 | Hatlestad |
| 2010/0139660 A1 | 6/2010 | Adahan |
| 2010/0145165 A1 | 6/2010 | Merry |
| 2010/0145201 A1 | 6/2010 | Westbrook et al. |
| 2010/0147303 A1 | 6/2010 | Jafari et al. |
| 2010/0152553 A1 | 6/2010 | Ujhazy et al. |
| 2010/0152560 A1 | 6/2010 | Turcott |
| 2010/0170512 A1 | 7/2010 | Kuypers et al. |
| 2010/0174200 A1 | 7/2010 | Wood et al. |
| 2010/0174207 A1 | 7/2010 | Lee et al. |
| 2010/0180898 A1 | 7/2010 | Schneider et al. |
| 2010/0186741 A1 | 7/2010 | Aylsworth et al. |
| 2010/0186742 A1 | 7/2010 | Sherman et al. |
| 2010/0186743 A1 | 7/2010 | Kane et al. |
| 2010/0186744 A1 | 7/2010 | Andrieux |
| 2010/0191076 A1 | 7/2010 | Lewicke et al. |
| 2010/0191137 A1 | 7/2010 | Brada et al. |
| 2010/0192094 A1 | 7/2010 | Jeha et al. |
| 2010/0198086 A1 | 8/2010 | Kuo et al. |
| 2010/0198289 A1 | 8/2010 | Kameli et al. |
| 2010/0199991 A1 | 8/2010 | Koledin |
| 2010/0210924 A1 | 8/2010 | Parthasarathy et al. |
| 2010/0212675 A1 | 8/2010 | Walling et al. |
| 2010/0218764 A1 | 9/2010 | Kwok et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0218773 A1 | 9/2010 | Thornton |
| 2010/0222692 A1 | 9/2010 | McCawley et al. |
| 2010/0222693 A1 | 9/2010 | Eriksen et al. |
| 2010/0224190 A1 | 9/2010 | Tilley et al. |
| 2010/0228133 A1 | 9/2010 | Averina et al. |
| 2010/0228134 A1 | 9/2010 | Martikka et al. |
| 2010/0229863 A1 | 9/2010 | Enk |
| 2010/0234750 A1 | 9/2010 | Ariav et al. |
| 2010/0236553 A1* | 9/2010 | Jafari ............... A61M 16/0051 128/204.21 |
| 2010/0236554 A1 | 9/2010 | Prete |
| 2010/0236555 A1* | 9/2010 | Jafari ............... A61M 16/0051 128/204.23 |
| 2010/0241009 A1 | 9/2010 | Petkie |
| 2010/0242961 A1 | 9/2010 | Mougel et al. |
| 2010/0242965 A1 | 9/2010 | Berthon-Jones |
| 2010/0249549 A1 | 9/2010 | Baker, Jr. et al. |
| 2010/0249630 A1 | 9/2010 | Droitcour et al. |
| 2010/0249631 A1 | 9/2010 | Aoki et al. |
| 2010/0249632 A1 | 9/2010 | Lee et al. |
| 2010/0249633 A1 | 9/2010 | Droitcour et al. |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0256463 A1 | 10/2010 | Greenwald et al. |
| 2010/0258116 A1 | 10/2010 | Federspiel et al. |
| 2010/0258124 A1 | 10/2010 | Madaus et al. |
| 2010/0258126 A1 | 10/2010 | Ujhazy et al. |
| 2010/0258127 A1 | 10/2010 | Hk |
| 2010/0262032 A1 | 10/2010 | Freeberg |
| 2010/0262035 A1 | 10/2010 | Subramanian |
| 2010/0275920 A1 | 11/2010 | Tham et al. |
| 2010/0282251 A1 | 11/2010 | Calluaud et al. |
| 2010/0282259 A1 | 11/2010 | Figueiredo et al. |
| 2010/0288279 A1 | 11/2010 | Seiver et al. |
| 2010/0288283 A1 | 11/2010 | Campbell et al. |
| 2010/0292544 A1 | 11/2010 | Sherman et al. |
| 2010/0300446 A1 | 12/2010 | Nicolazzi et al. |
| 2010/0324438 A1 | 12/2010 | Ni et al. |
| 2010/0331639 A1 | 12/2010 | O'Reilly |
| 2010/0331715 A1 | 12/2010 | Addison et al. |
| 2011/0009763 A1 | 1/2011 | Levitsky et al. |
| 2011/0011400 A1 | 1/2011 | Gentner et al. |
| 2011/0017214 A1 | 1/2011 | Tehrani |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0036352 A1 | 2/2011 | Estes et al. |
| 2011/0041847 A1 | 2/2011 | Cosic |
| 2011/0041849 A1 | 2/2011 | Chen et al. |
| 2011/0041850 A1* | 2/2011 | Vandine ............ A61M 16/0051 128/204.23 |
| 2011/0067698 A1 | 3/2011 | Zheng et al. |
| 2011/0092839 A1 | 4/2011 | Alshaer et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |

(56) References Cited

U.S. PATENT DOCUMENTS

| | | | |
|---|---|---|---|
| 2011/0175728 A1* | 7/2011 | Baker, Jr. | A61M 16/0051 340/540 |
| 2011/0196251 A1 | 8/2011 | Jourdain et al. | |
| 2011/0197884 A1 | 8/2011 | Duff et al. | |
| 2011/0208082 A1 | 8/2011 | Madaus et al. | |
| 2011/0209702 A1 | 9/2011 | Vuong et al. | |
| 2011/0209704 A1 | 9/2011 | Jafari et al. | |
| 2011/0209707 A1 | 9/2011 | Terhark | |
| 2011/0213215 A1 | 9/2011 | Doyle et al. | |
| 2011/0230780 A1 | 9/2011 | Sanborn et al. | |
| 2011/0249006 A1 | 10/2011 | Wallace et al. | |
| 2011/0259330 A1 | 10/2011 | Jafari et al. | |
| 2011/0259332 A1* | 10/2011 | Sanchez et al. | 128/204.21 |
| 2011/0259333 A1 | 10/2011 | Sanchez et al. | |
| 2011/0265024 A1 | 10/2011 | Leone et al. | |
| 2011/0265793 A1 | 11/2011 | Haveri | |
| 2011/0271960 A1 | 11/2011 | Milne et al. | |
| 2011/0273299 A1 | 11/2011 | Milne et al. | |
| 2011/0288431 A1 | 11/2011 | Alshaer et al. | |
| 2011/0313263 A1 | 12/2011 | Wood et al. | |
| 2012/0000467 A1 | 1/2012 | Milne et al. | |
| 2012/0000468 A1 | 1/2012 | Milne et al. | |
| 2012/0000469 A1 | 1/2012 | Milne et al. | |
| 2012/0000470 A1 | 1/2012 | Milne et al. | |
| 2012/0016252 A1 | 1/2012 | Melker et al. | |
| 2012/0029317 A1 | 2/2012 | Doyle et al. | |
| 2012/0029362 A1 | 2/2012 | Patangay et al. | |
| 2012/0030611 A1 | 2/2012 | Skidmore | |
| 2012/0037159 A1 | 2/2012 | Mulqueeny et al. | |
| 2012/0060841 A1 | 3/2012 | Crawford, Jr. et al. | |
| 2012/0071729 A1 | 3/2012 | Doyle et al. | |
| 2012/0090611 A1 | 4/2012 | Graboi et al. | |
| 2012/0096381 A1 | 4/2012 | Milne et al. | |
| 2012/0101399 A1 | 4/2012 | Henderson | |
| 2012/0123219 A1 | 5/2012 | Georgiev et al. | |
| 2012/0133519 A1 | 5/2012 | Milne et al. | |
| 2012/0136222 A1 | 5/2012 | Doyle et al. | |
| 2012/0136270 A1 | 5/2012 | Leuthardt et al. | |
| 2012/0137249 A1 | 5/2012 | Milne et al. | |
| 2012/0137250 A1 | 5/2012 | Milne et al. | |
| 2012/0167885 A1 | 7/2012 | Masic et al. | |
| 2012/0185792 A1 | 7/2012 | Kimm et al. | |
| 2012/0197578 A1 | 8/2012 | Vig et al. | |
| 2012/0197580 A1 | 8/2012 | Vij et al. | |
| 2012/0211008 A1 | 8/2012 | Perine et al. | |
| 2012/0216809 A1 | 8/2012 | Milne et al. | |
| 2012/0216810 A1 | 8/2012 | Jafari et al. | |
| 2012/0216811 A1 | 8/2012 | Kimm et al. | |
| 2012/0226444 A1* | 9/2012 | Milne | A61B 5/08 702/19 |
| 2012/0247471 A1 | 10/2012 | Masic et al. | |
| 2012/0272960 A1 | 11/2012 | Milne | |
| 2012/0272961 A1 | 11/2012 | Masic et al. | |
| 2012/0272962 A1 | 11/2012 | Doyle et al. | |
| 2012/0277616 A1 | 11/2012 | Sanborn et al. | |
| 2012/0279501 A1 | 11/2012 | Wallace et al. | |
| 2012/0304995 A1 | 12/2012 | Kauc | |
| 2012/0304997 A1 | 12/2012 | Jafari et al. | |
| 2013/0000644 A1 | 1/2013 | Thiessen | |
| 2013/0006133 A1 | 1/2013 | Doyle et al. | |
| 2013/0006134 A1 | 1/2013 | Doyle et al. | |
| 2013/0008443 A1 | 1/2013 | Thiessen | |
| 2013/0025596 A1 | 1/2013 | Jafari et al. | |
| 2013/0025597 A1 | 1/2013 | Doyle et al. | |
| 2013/0032149 A1* | 2/2013 | Robinson | A61B 5/08 128/204.21 |
| 2013/0032151 A1 | 2/2013 | Adahan | |
| 2013/0042869 A1 | 2/2013 | Andrieux et al. | |
| 2013/0047983 A1 | 2/2013 | Andrieux et al. | |
| 2013/0047989 A1 | 2/2013 | Vandine et al. | |
| 2013/0053717 A1 | 2/2013 | Vandine et al. | |
| 2013/0074844 A1 | 3/2013 | Kimm et al. | |
| 2013/0081536 A1 | 4/2013 | Crawford, Jr. et al. | |
| 2013/0104896 A1 | 5/2013 | Kimm et al. | |
| 2013/0146055 A1 | 6/2013 | Jafari et al. | |
| 2013/0152923 A1 | 6/2013 | Andrieux et al. | |
| 2013/0152934 A1* | 6/2013 | Mulqueeny | A61M 16/0051 128/204.23 |
| 2013/0158370 A1 | 6/2013 | Doyle et al. | |
| 2013/0159912 A1 | 6/2013 | Baker, Jr. | |
| 2013/0167842 A1 | 7/2013 | Jafari et al. | |
| 2013/0167843 A1 | 7/2013 | Kimm et al. | |
| 2013/0186397 A1 | 7/2013 | Patel | |
| 2013/0186400 A1 | 7/2013 | Jafari et al. | |
| 2013/0186401 A1 | 7/2013 | Jafari et al. | |
| 2013/0192599 A1 | 8/2013 | Nakai et al. | |
| 2013/0220324 A1 | 8/2013 | Jafari et al. | |
| 2013/0233314 A1 | 9/2013 | Jafari et al. | |
| 2013/0233319 A1 | 9/2013 | Winter et al. | |
| 2013/0239038 A1 | 9/2013 | Skidmore et al. | |
| 2013/0239967 A1 | 9/2013 | Jafari et al. | |
| 2013/0255682 A1 | 10/2013 | Jafari et al. | |
| 2013/0255685 A1 | 10/2013 | Jafari et al. | |
| 2013/0276788 A1 | 10/2013 | Masic | |
| 2013/0283197 A1 | 10/2013 | Skidmore | |
| 2013/0284173 A1 | 10/2013 | Masic et al. | |
| 2013/0327331 A1 | 12/2013 | Bourdon | |
| 2013/0333697 A1 | 12/2013 | Carter et al. | |
| 2013/0333703 A1 | 12/2013 | Wallace et al. | |
| 2013/0338514 A1 | 12/2013 | Karst et al. | |
| 2013/0345532 A1 | 12/2013 | Doyle et al. | |
| 2014/0034056 A1 | 2/2014 | Leone et al. | |
| 2014/0123979 A1 | 5/2014 | Doyle et al. | |
| 2014/0182590 A1 | 7/2014 | Platt et al. | |
| 2014/0224250 A1 | 8/2014 | Sanchez et al. | |
| 2014/0251328 A1 | 9/2014 | Graboi et al. | |
| 2014/0261409 A1 | 9/2014 | Dong et al. | |
| 2014/0261410 A1 | 9/2014 | Sanchez et al. | |
| 2014/0261424 A1 | 9/2014 | Doyle et al. | |
| 2014/0276176 A1 | 9/2014 | Winter | |
| 2014/0373845 A1 | 12/2014 | Dong | |
| 2015/0034082 A1 | 2/2015 | Kimm et al. | |
| 2015/0045687 A1 | 2/2015 | Nakai et al. | |

FOREIGN PATENT DOCUMENTS

| | | |
|---|---|---|
| EP | 858352 | 1/2005 |
| EP | 1515767 | 8/2009 |
| WO | WO 9014852 | 12/1990 |
| WO | WO 9214505 | 9/1992 |
| WO | WO 9308857 | 5/1993 |
| WO | WO 199715343 | 5/1997 |
| WO | WO 9812965 | 4/1998 |
| WO | WO 199951292 | 10/1999 |
| WO | WO 199962580 | 12/1999 |
| WO | WO 200010634 | 3/2000 |
| WO | WO 200078380 | 12/2000 |
| WO | WO 0100264 | 1/2001 |
| WO | WO 0100265 | 1/2001 |
| WO | WO 200174430 | 10/2001 |
| WO | WO 2002028460 | 4/2002 |
| WO | WO 2002032488 | 4/2002 |
| WO | WO 2003008027 | 1/2003 |
| WO | WO 04000114 | 12/2003 |
| WO | WO 04047621 | 6/2004 |
| WO | WO 2005004780 | 1/2005 |
| WO | WO 0785110 | 8/2007 |
| WO | WO 2007102866 | 9/2007 |
| WO | WO 2007145948 | 12/2007 |

OTHER PUBLICATIONS

7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1988, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.

(56) References Cited

OTHER PUBLICATIONS

Carteaux, G. et al., "An Algorithm to Adjust the Percentage of Assistance in PAV+ Based on an Estimation of the Patient's Respiratory Effort", Am. J. Respir. Crit. Care Med. 181, 2010, 1 pg. abstract.

* cited by examiner

METHODS AND SYSTEMS FOR AN OPTIMIZED PROPORTIONAL ASSIST VENTILATION

INTRODUCTION

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes or settings have been created to provide better ventilation for patients in various different scenarios.

Optimized Proportional Assist Ventilation

This disclosure describes systems and methods for providing an optimized proportional assist breath type during ventilation of a patient. The disclosure describes a novel breath type that delivers a target airway pressure calculated based on a desired patient effort range to a triggering patient.

In part, this disclosure describes a method for ventilating a patient with a ventilator. The method includes:
 a) retrieving a desired patient effort range;
 b) estimating an initial percent support setting based on the desired patient effort range;
 c) calculating a target airway pressure based at least on the initial percent support setting; and
 d) delivering the target airway pressure to a patient.

Yet another aspect of this disclosure describes a ventilator system that includes: a pressure generating system; a ventilation tubing system; one or more sensors; a support module; and an OPA module. The pressure generating system is adapted to generate a flow of breathing gas. The ventilation tubing system includes a patient interface for connecting the pressure generating system to a patient. The one or more sensors are operatively coupled to at least one of the pressure generating system, the patient, and the ventilation tubing system. The one or more sensors generate output indicative of the inspiration flow. The support module estimates an initial percent support setting based at least on a desired patient effort range and calculates at least one adjusted percent support setting based at least on the desired patient effort range, and a current patient effort. The OPA module calculates an initial target airway pressure based at least on the initial percent support setting, calculates at least one adjusted target airway pressure based at least on an adjusted percent support setting, and utilizes the output indicative of the inspiration flow to determine a patient trigger for delivery of a breath to the patient.

The disclosure further describes a computer-readable medium having computer-executable instructions for performing a method for ventilating a patient with a ventilator. The method includes:
 a) repeatedly retrieving a desired patient effort range;
 b) estimating an initial percent support setting based on the desired patient effort range;
 c) repeatedly calculating a target airway pressure based at least on the initial percent support setting; and
 d) repeatedly delivering the target airway pressure to a patient.

The disclosure also describes a ventilator system including means for retrieving a desired patient effort range, means for estimating an initial percent support setting based on the desired patient effort range, means for calculating a target airway pressure based at least on the initial percent support setting, and means for delivering the target airway pressure to a patient.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims appended hereto.

DETAILED DESCRIPTION

Figure 1:
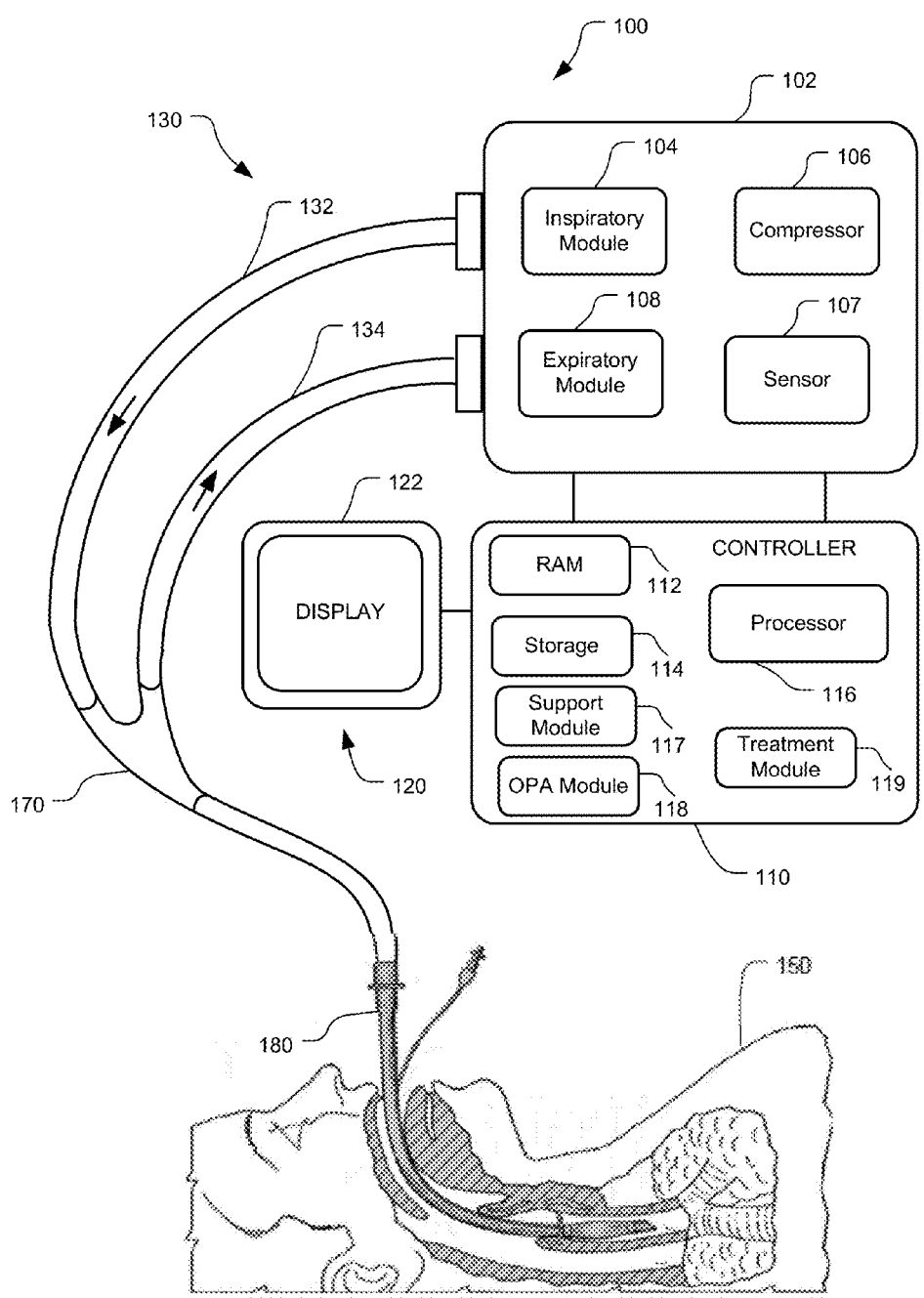
FIG. 1 illustrates an embodiment of a ventilator.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

While operating a ventilator, it is desirable to control the percentage of oxygen in the gas supplied by the ventilator to the patient. Further, as each patient may require a different ventilation strategy, modern ventilators can be customized for the particular needs of an individual patient. For example, several different ventilator breath types have been created to provide better ventilation for patients in various different scenarios.

Effort-based breath types, such as proportional assist (PA) ventilation, dynamically determine the amount of ventilatory support to deliver based on a continuous estimation/calculation of patient effort and respiratory characteristics. The resulting dynamically generated profile is computed in real- or quasi-real-time and used by the ventilator as a set of points for control of applicable parameters.

Initiation and execution of an effort-based breath, such as PA, has two operation prerequisites: (1) detection of an inspiratory trigger; and (2) detection and measurement of an appreciable amount of patient respiratory effort to constitute a sufficient reference above a ventilator's control signal error deadband. Advanced, sophisticated triggering technologies detect initiation of inspiratory efforts efficiently. In ventilation design, patient effort may be represented by the estimated inspiratory muscle pressure (patient effort) and is calculated based on measured patient inspiration flow. Patient effort is utilized to calculate a target airway pressure for the inspiration. The target airway pressure as used herein is the airway pressure measured at the ventilator-patient interface and is calculated on an on-going basis using patient effort according to the equation of motion. In other words, the target airway pressure is the amount of pressure delivered by the ventilator to the patient.

A PA breath type refers to a type of ventilation in which the ventilator acts as an inspiratory amplifier that provides pressure support based on the patient's effort. The degree of amplification (the "percent support setting") during a PA breath type is set by an operator, for example as a percentage based on the patient's effort. In one implementation of a PA breath type, the ventilator may continuously monitor the patient's instantaneous inspiratory flow and instantaneous net lung volume, which are indicators of the patient's inspiratory effort. These signals, together with ongoing estimates of the patient's lung compliance and lung/airway resistance and the Equation of Motion (Target Pressure(t)=$E_p \int Q_p dt + Q_p R_p$−Patient Effort(t)), allow the ventilator to estimate/calculate a patient effort and derive therefrom a target airway pressure to provide the support that assists the patient's inspiratory muscles to the degree selected by the operator as the percent support setting. $Q_p$ is the instantaneous flow inhaled by the patient, and $E_p$ and $R_Q$ are the patient's respiratory elastance and resistance, respectively. In this equation the patient effort is inspiratory muscle pressure and is negative. The percent support setting input by the operator divides the total work of breathing calculated between the patient and the ventilator as shown in the equations below:

Patient Effort(t)=(1.0−k)[$E_p \int Q_p dt + Q_p R_p$];      1) and

Target Airway Pressure(t)=k[$E_p \int Q_p dt + Q_p R_p$].      2)

Patient Effort(t) is the amount of pressure provided by the patient at a time t, Target airway pressure(t) is the amount of pressure provided by the ventilator at the time t, total support ([$E_p \int Q_p dt + Q_p R_p$]) is the sum of contributions by the patient and ventilator, and k is the percent support setting (percentage of total support to be contributed by the ventilator) input by the operator.

During PA breath types, the percent support setting is input by the operator of the ventilator and does not vary. Clinicians, typically, do not utilize a percent support setting unless operating a PA breath type. Accordingly, often times, clinicians or ventilator operators are unfamiliar with a percent support setting and need additional training to learn how to use a proportional assist breath type appropriately. Further, during the previously utilized PA breath types, the patient effort was only estimated/calculated. The ventilator did not attempt to control or change the amount of effort exerted by the patient. Accordingly, the patient could exert too much effort resulting in fatigue from over-loading or the patient could exert too little effort leading to muscle atrophy from non-use.

Researchers have discovered that maintaining a desired patient effort can provide the patient with several benefits. For example, certain patient efforts prevent muscle atrophy from non-use while at the same time prevent muscle fatigue from over-loading. Further, controlling and/or adjusting a patient's effort can also help to maintain a desired treatment metric range.

Accordingly, the current disclosure describes an optimized proportional assist (OPA) breath type for ventilating a patient. The OPA breath type is similar to the PA breath type except that the OPA breath type delivers a target airway pressure to the patient calculated based on a desired patient effort range for a triggering patient instead of being based on an input percent support setting. Accordingly, the ventilator estimates an initial percent support setting during the OPA breath type in an attempt to achieve a patient effort in the desired range. The target airway pressure delivered to the patient is calculated based on the estimated initial percent support setting. After the delivery of the target airway pressure based on the estimated initial percent support setting, the ventilator periodically calculates/estimates the actual amount of patient effort or the current patient effort exerted by the patient. The ventilator compares the current patient effort to the desired patient effort range. If the current the patient effort is not within the desired patient effort range, the ventilator modifies the percent support setting in an attempt to deliver a target airway pressure that will cause the patient to exert a patient effort in the desired patient effort range in the next breath. In some embodiments, the desired patient effort range is input or selected by the operator of the ventilator. Most clinicians are familiar with patient effort levels. Accordingly, an OPA breath type requires minimal training or education for proper use by clinicians. Further, the OPA breath type allows clinicians to better manage the patient's contribution to the total work of breathing.

Additionally, in some embodiments, the ventilator during the OPA breath type may determine the desired patient effort range based on a desired treatment metric range. The desired treatment metric range (e.g., a rapid shallow breathing index (RSBI) range) is input or selected by the operator. In these embodiments, the percent support setting is adjusted until the current patient effort is maintained within the desired patient effort range for at least two consecutive breaths. Once the current patient effort is maintained within the desired patient effort range, one or more ventilator parameters (e.g., positive end expiratory pressure (PEEP), rise time, and oxygen percentage) and/or their derivatives (e.g., windowed history, trends, windowed statistics, rate of change with respect to other factors, and etc.) are adjusted until the current treatment metric and/or their derivatives (e.g., windowed history, trends, windowed statistics, rate of change with respect to other factors, and etc.) is within the desired treatment metric range.

As used herein, patient parameters are any parameters determined based on measurements taken of the patient, such as heart rate, respiration rate, a blood oxygen level (SpO$_2$), inspiratory lung flow, airway pressure, and etc. As used herein, ventilator parameters are parameters that are determined by the ventilator and/or are input into the ventilator by an operator, such as a breath type, desired patient effort, and etc. Some parameters may be either ventilator and/or patient parameters depending upon whether or not they are input into the ventilator by an operator or determined by the ventilator. Accordingly, the treatment metric is a ventilator parameter.

The percent support setting and the ventilator parameters are adjusted based on algorithms and optimization programming techniques to provide advisory input and/or automatic adjustments to ventilation parameters (e.g., percent support in OPA) and/or a timed changes in ventilation modality (patient-triggered or ventilator-driven breath delivery) to increase the efficiency and confidence in the predictive nature of the desired treatment metric range. In other words, the algorithms and optimization programming techniques adjust the percent support setting and one or more ventilator parameters in an attempt to get the current treatment metric within the desired treatment metric range.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 according to prescribed ventilatory settings. In some embodiments, inspiratory module 104 is configured to provide ventilation according to various breath types, e.g., via volume-control, pressure-control, OPA, or via any other suitable breath types.

The expiratory module 108 is configured to release gases from the patient's lungs according to prescribed ventilatory settings. Specifically, expiratory module 108 is associated with and/or controls an expiratory valve for releasing gases from the patient 150.

The ventilator 100 may also include one or more sensors 107 communicatively coupled to ventilator 100. The sensors 107 may be located in the pneumatic system 102, ventilation tubing system 130, and/or on the patient 150. The embodiment of FIG. 1 illustrates a sensor 107 in pneumatic system 102.

Sensors 107 may communicate with various components of ventilator 100, e.g., pneumatic system 102, other sensors 107, processor 116, support module 117, OPA module 118, and any other suitable components and/or modules. In one embodiment, sensors 107 generate output and send this output to pneumatic system 102, other sensors 107, processor 116, support module 117, OPA module 118, treatment module 119 and any other suitable components and/or modules. Sensors 107 may employ any suitable sensory or derivative technique for monitoring one or more patient parameters or ventilator parameters associated with the ventilation of a patient 150. Sensors 107 may detect changes in patient parameters indicative of patient triggering, for example. Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or expiratory modules for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in or near wye-fitting 170 and/or patient interface 180. Indeed, any sensory device useful for monitoring changes in measurable parameters during ventilatory treatment may be employed in accordance with embodiments described herein.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored or estimated/calculated using a model, such as a model derived from the Equation of Motion (e.g., Target Airway Pressure(t)=$E_p \int Q_p dt + Q_p R_p$ − Patient Effort(t)).

The pneumatic system 102 may include a variety of other components, including mixing modules, valves, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122. Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In one embodiment, the display 122 may display one or more of a current patient effort, a desired patient effort range, a desired treatment metric range, a current treatment metric, a RSBI, SpO$_2$, a mouth pressures measured at 100 milliseconds (ms) after the onset of inspiratory effort (P$_{100}$), a tidal volume, a volumetric carbon dioxide (VCO$_2$), a respiratory rate, a spontaneous inspiration to expiration ratio (I:E) volume, a minute volume, an initial percent support setting, and an adjusted percent support setting.

Controller 110 may include memory 112, one or more processors 116, storage 114, and/or other components of the type commonly found in command and control computing devices. Controller 110 may further include a support module 117, an OPA module 118, and treatment module 119 configured to deliver gases to the patient 150 according to prescribed breath types as illustrated in FIG. 1. In alternative embodiments, the support module 117, the OPA module 118, and the treatment module 119 may be located in other components of the ventilator 100, such as the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The inspiratory module 104 receives a breath type from the OPA module 118. The OPA module 118 receives a percent support setting for the breath type from the support module 117. In some embodiments, the OPA module 118 and/or the support module 117 are part of the controller 110 as illustrated in FIG. 1. In other embodiments, the OPA module 118 and/or the support module 117 are part of the processor 116, pneumatic system 102, and/or a separate computing device in communication with the ventilator 100.

Initiation and execution of an OPA breath type has two operation prerequisites: (1) detection of an inspiratory trigger; and (2) determining and commanding target airway pressures to be delivered to the patient 150 during inspiration. A patient trigger is calculated based on a measured or monitored patient inspiration flow. Any suitable type of triggering detection for determining a patient trigger may be utilized by the ventilator 100, such as nasal detection, diaphragm detection, and/or brain signal detection. Further, the ventilator 100 may detect patient triggering via a pressure-monitoring method, a flow-monitoring method, direct or indirect measurement of neuromuscular signals, or any other suitable method. Sensors 107 suitable for this detection may include any suitable sensing device as known by a person of skill in the art for a ventilator.

According to an embodiment, a pressure-triggering method may involve the ventilator 100 monitoring the circuit pressure, and detecting a slight drop in circuit pressure. The slight drop in circuit pressure may indicate that the patient's respiratory muscles are creating a slight negative pressure that in turn generates a pressure gradient between the patient's lungs and the airway opening in an effort to inspire. The ventilator 100 may interpret the slight drop in circuit pressure as a patient trigger and may consequently initiate inspiration by delivering respiratory gases.

Alternatively, the ventilator 100 may detect a flow-triggered event. Specifically, the ventilator 100 may monitor the circuit flow, as described above. If the ventilator 100 detects a slight drop in the base flow through the exhalation module during exhalation, this may indicate, again, that the patient 150 is attempting to inspire. In this case, the ventilator 100 is detecting a drop in bias flow (or baseline flow) attributable to a slight redirection of gases into the patient's lungs (in response to a slightly negative pressure gradient as discussed above). Bias flow refers to a constant flow existing in the circuit during exhalation that enables the ventilator 100 to detect expiratory flow changes and patient triggering.

The OPA module 118 sends an OPA breath type to the inspiratory module 104. The OPA breath type refers to a type of ventilation in which the ventilator 100 acts as an inspiratory amplifier that provides pressure support to the patient. The degree of amplification (the "percent support setting") is determined by the support module 117 based on a retrieved desired patient effort range. The percent support setting determines how much support is provided by the ventilator 100. For example, if the percent support setting is 30%, then the ventilator provides a total pressure to the patient of which 70% is due to the patient effort (generation of muscle pressure) and the remaining 30% is due to the ventilator work, as estimated from the instantaneous flow or other monitored parameters based on the patient effort model used.

In an embodiment, the OPA breath type determines a target airway pressure by utilizing the percent support setting and the following equation:

$$\text{Target Airway Pressure}(t) = k[E_p \int Q_p dt + Q_p R_p]$$

The percent support setting (k) is held constant over one breath. Every computational cycle (e.g., 5 milliseconds, 10 milliseconds, etc.), the ventilator calculates a target airway pressure, based on the received percent support setting from the support module 117.

The OPA module 118 begins inspiratory assist when a trigger is detected and/or when the at least one monitored parameter is detected by the OPA module 118. However, if the patient ceases triggering inspiration, the assist also ceases. Accordingly, in some embodiments, the OPA module 118 includes a safety feature that has the ventilator 100 deliver a breath to the patient or switches the breath type to a non-spontaneous breath type if a patient trigger is not detected for a set period of time or based on the occurrence of a set event. This safety feature ensures that if a patient stops triggering, the patient will not stop receiving ventilation by the medical ventilator.

The support module 117 retrieves a desired patient effort range for the OPA breath type. The desired patient effort range represents a desired parameter from the patient effort profile over each breath. The desired patient effort may be a maximum, mean, root mean square (RMS), minimum or any other appropriate statistic of the a pressure waveform or patient muscle waveform during one or a window of multiple breaths. The desired patient effort range (such as a desired peak muscle pressure) may be retrieved from input or a selection by the operator of the ventilator 100 or may be retrieved from a determination made by the ventilator 100. The ventilator 100 may determine the desired patient effort range based on patient parameters and/or ventilator parameters. In some embodiments, the support module 117 receives the desired patient effort range from the treatment module 119, processor 116, and/or operator interface 120.

The desired patient effort range is a range of patient effort that should provide benefits to the patient. In some embodiments, the desired patient effort range prevents muscle atrophy from non-use while at the same time prevents muscle fatigue from over-loading. In further embodiments, determining a desired patient effort range based on a desired treatment metric range in combination with adjusting one or more ventilator parameters to maintain a current treatment metric in the desired treatment metric range to improve the ventilator's treatments of certain conditions, such as reducing the amount of time the ventilator takes to wean a patient from ventilation.

In some embodiments, the desired patient effort range is from about 5 cm $H_2O$ to about 10 cm of $H_2O$. In other embodiments, the desired patient effort range is from about 4 cm $H_2O$ to about 12 cm of $H_2O$. In some embodiments, the desired patient effort range is from about 6 cm $H_2O$ to about 9 cm of $H_2O$. The desired patient effort range may include a solitary value. Accordingly, the desired patient effort range may be 5 cm of $H_2O$, 6 cm of $H_2O$, 7 cm of $H_2O$, 8 cm of $H_2O$, 9 cm of $H_2O$, or 10 cm of $H_2O$. These lists are not meant to be limiting. Any suitable patient effort range for improving the health of the patient may be utilized by the ventilator 100.

The support module 117 utilizes the retrieved desired patient effort range to estimate an initial percent support setting. The initial percent support setting as used herein is the percent support setting applied to at least the first breath delivered to the patient during execution of the OPA breath type. The support module 117 estimates the initial percent support setting, k, by utilizing the follow equation based on the equation of motion when given the other parameters:

$$\text{Patient Effort}(t) = (1.0-k)[E_p \int Q_p dt + Q_p R_p].$$

The ventilator utilizes an initial support setting and predetermined settings for the remaining parameters that cannot be determined since this is the first delivered breath. The predetermined settings may vary based on other parameters input by the clinician.

The support module 117 sends the initial percent support setting to the OPA module 118. As discussed above, the OPA module 118 then utilizes the initial percent support setting to calculate an initial target airway pressure to deliver to the patient 150. The OPA module 118 then causes the ventilator 100 to deliver the initial target airway pressure in at least the first breath provided to the patient during the utilization of the OPA breath type. Accordingly, the OPA module 118 may send the target airway pressure and/or instruction for delivering the target airway pressure to at least one of the processor 116, pneumatic system 102, inspiratory module 104 and/or the controller 110.

After the delivery of the first breath during the OPA breath type, the ventilator 100 calculates the current or actual patient effort exerted by the patient during the first breath and calculates the current patient effort periodically after the first delivered breath. Any component of the ventilator 100 may perform this step, such as the pneumatic system 102, controller 110, processor 116, support module 117, or OPA module 118. For example, the ventilator 100 may calculate the current patient effort for every delivered breath or every breath delivered after a predetermined amount of time or after a predetermined event. The current patient effort or actual patient effort as used herein represents the amount of patient effort exerted by the patient within the last computational cycle for the last delivered breath. The current patient effort is calculated based on the equation of motion and estimated patient parameters. The parameter representing the actual patient effort may be derived from the calculated patient effort profile over each breath. It may be defined as the maximum, mean, root mean square (RMS), or any other appropriate statistic of the actual muscle pressure waveform during one or a window of multiple breaths. The ventilator 100 estimates patient parameters based on the measurements directly or indirectly related to monitored patient parameters. In some embodiments, the estimated patient parameters include lung compliance (inverse of elastance) and/or lung/airway resistance. In further embodiments, the estimated lung compliance, lung elastance and/or lung/airway resistance are estimated based on monitored flow and/or the equation of motion. The estimated patient parameters may be estimated by any processor found in the ventilator 100. In some embodiments, the estimated patient parameters are calculated by the controller 110, the pneumatic system 102, and/or a separate computing device operatively connected to the ventilator 100.

In one embodiment, the support module 117 or any other suitable ventilator component compares the current patient effort with the desired patient effort range. If the support module 117 or any other suitable ventilator component determines that the actual or current patient effort is within the desired patient effort range, the support module 117 after receiving notification that or after determining that the current patient effort in within the desired patient effort range, sends the previously utilized percent support setting to the OPA module 118. In some instances, the previously utilized percent support setting may be the initial percent support setting. If the support module 117 or any other suitable ventilator component determines that the current patient effort is outside of the desired patient effort range, the support module 117 after receiving notification that or after determining that the current patient effort in not within the desired patient effort range, utilizes an optimization algorithm to adjust the percent support setting. Example optimization algorithms are listed below in the example section. The adjusted percent support setting (k) is held constant over one breath. The support module 117 sends the adjusted percent support setting to the OPA module 118. The OPA module 118, as discussed above, calculates the target airway pressure based on the percent support setting received from the support module 117, whether the percent support setting is an adjusted percent support setting, an initial percent support setting, and/or the previously utilized percent support setting. As discussed above, the target pressure is calculated every control cycle using the adjusted percent support setting by the ventilator 100.

Determining a desired patient effort based on desired treatment metric range can improve patient treatment, such as reducing weaning time and minimizing lung injury. A treatment metric is a ventilator parameter that is indicative of how well a patient treatment is going. In some embodiments, the treatment metric includes RSBI, $SpO_2$, $P_{100}$, oxygen index, end tidal carbon dioxide (ETCO₂ or EtCO₂), tidal volume, VCO₂, respiratory rate, spontaneous I:E ratio, and a minute volume. The treatment module 119 receives a desired treatment metric range from the operator. The treatment module determines a desired patient effort range based on the received desired treatment metric range. The determined desired patient effort range is selected in attempt to help the patient achieve a current treatment metric within the desired treatment metric range. The treatment module sends the determined desired patient effort range to the appropriate ventilator component, such as the processor 116, support module 117 and/or the OPA module 118.

Once the ventilator 100 establishes a current patient effort within the desired patient effort range, the treatment module 119 determines if the current treatment metric is within the desired treatment metric range. The desired treatment metric range is a range of a ventilator parameter that improves the treatment of the patient. For example, if the treatment metric is RSBI, the desired treatment metric range may be a range of an RSBI of less than 105, which helps to decrease the amount of time a ventilator 100 takes to wean a patient 150 from ventilation. In some embodiments, the treatment metric range may not be a range and instead may be a solitary value, such as an RSBI of 100. The current treatment is metric as used herein represents the treatment metric as measured or determined by the ventilator 100 for the patient within the last computational cycle or for the last delivered breath depending upon the treatment metric utilized. In some embodiments, the treatment metric is derived from the calculated profiles over each breath. In some embodiments, the treatment metric is the maximum, mean, root mean square (RMS), or any other appropriate statistic of the waveform during one window or a window of multiple breaths.

In some embodiments, the treatment module 119 determines and adjusts the ventilator parameters and their derivatives based on weighted and/or trended desired treatment metric ranges input by the clinician. The treatment module 119 adjusts the percent support setting and the ventilator parameters by utilizing algorithms and optimization programming techniques to provide advisory input and/or automatic adjustments to ventilation parameters (e.g., oxygen percentage) and/or a timed changes in ventilation modality (patient-triggered or ventilator-driven breath delivery) to increase the efficiency and confidence in the predictive nature of the treatment success/failure indices. The ventilator parameters are adjusted based on treatment optimization algorithm. Example treatment optimization algorithms are listed below in the Example section. In other words, the algorithms and optimization programming techniques adjust the percent support setting and the one or more ventilator parameters in an attempt to improve patient treatment (i.e., maintain a current treatment metric within a desired treatment metric range).

The treatment module 119 sends the determined desired patient effort range to the support module 117. The support module 117 utilizes the determined desired patient effort range received from the treatment module 119 to calculate the percent support setting. The treatment module 119 sends the determined and/or adjusted one or more ventilator parameters to the appropriate component or components of the ventilator 100, such as the pneumatic system 102, controller 110, and/or processor 116, of the ventilator 100 for changing the one or more ventilator parameters.

In one embodiments, the treatment algorithm and/or optimization programming utilized by the treatment module 119 incorporates an internal model of the patient respiratory system in interaction with the ventilator 100 to address the relevant interactive dynamics between the patient 150 and the ventilator 100 as well as model and predict changes in patient's respiratory behavior and therapeutic outcome in response to the ongoing treatment protocol delivered by the ventilator 100. In some embodiments, the internal model for the treatment algorithm and/or optimization programming incorporates mechanisms for estimating system parameters (respiratory resistance, compliance, and etc.). Additionally, the treatment algorithm and/or the optimization programming utilized by the treatment module 119 may include features to estimate, model, or predict dynamics related to the functioning and interrelationships between inputs (e.g., percent support, SpO₂, oxygen mix, and etc.) and output (generated patient effort over time). In further embodiments, the treatment algorithm includes mechanisms to estimate physiologic-based and/or hardware-based dynamics (transients, delays, and etc.).

Figure 2A:
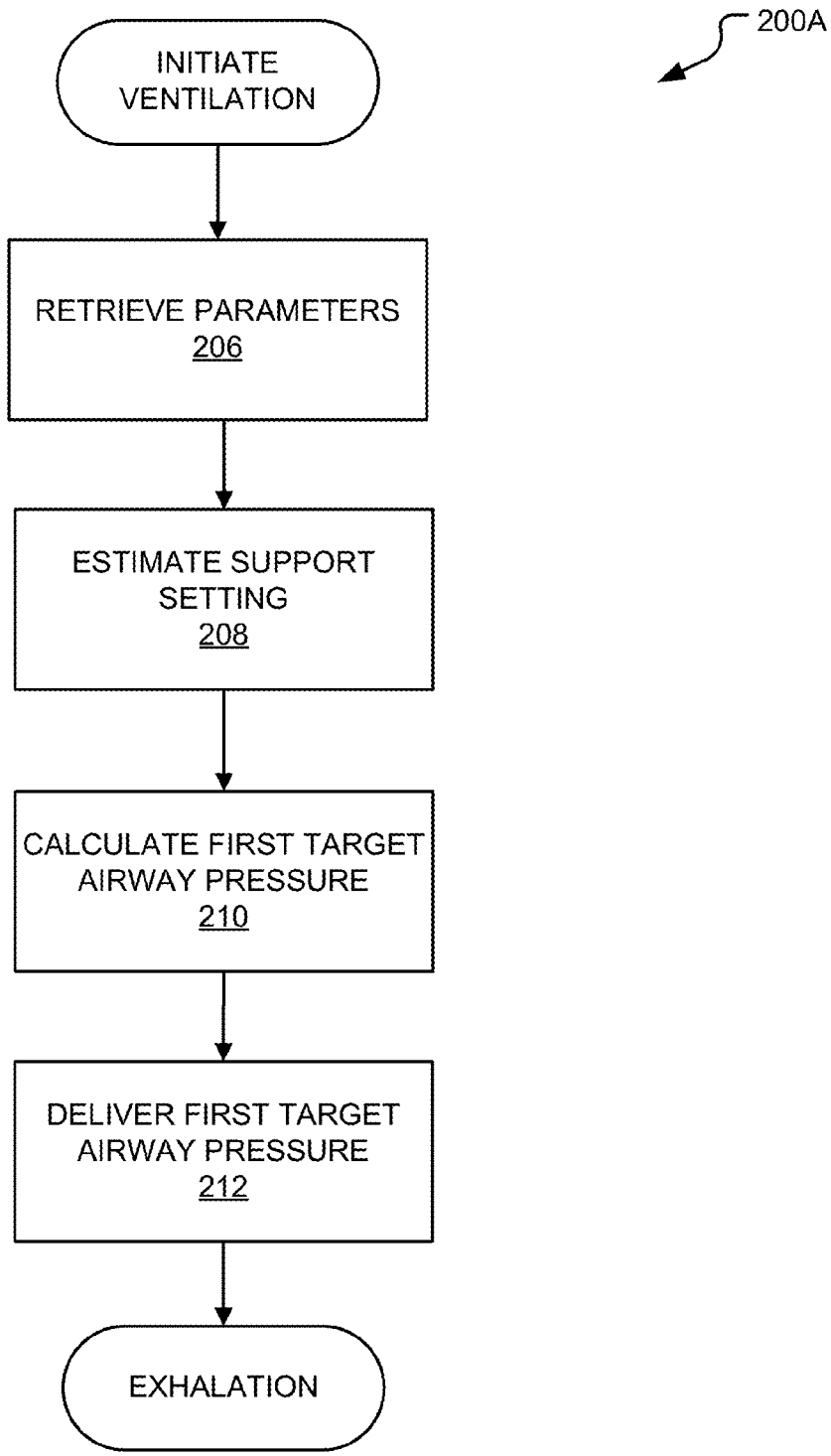
FIG. 2A illustrates an embodiment of a method for ventilating a patient on a ventilator during a first breath in an optimized proportional assist breath type.
Figure 2B:
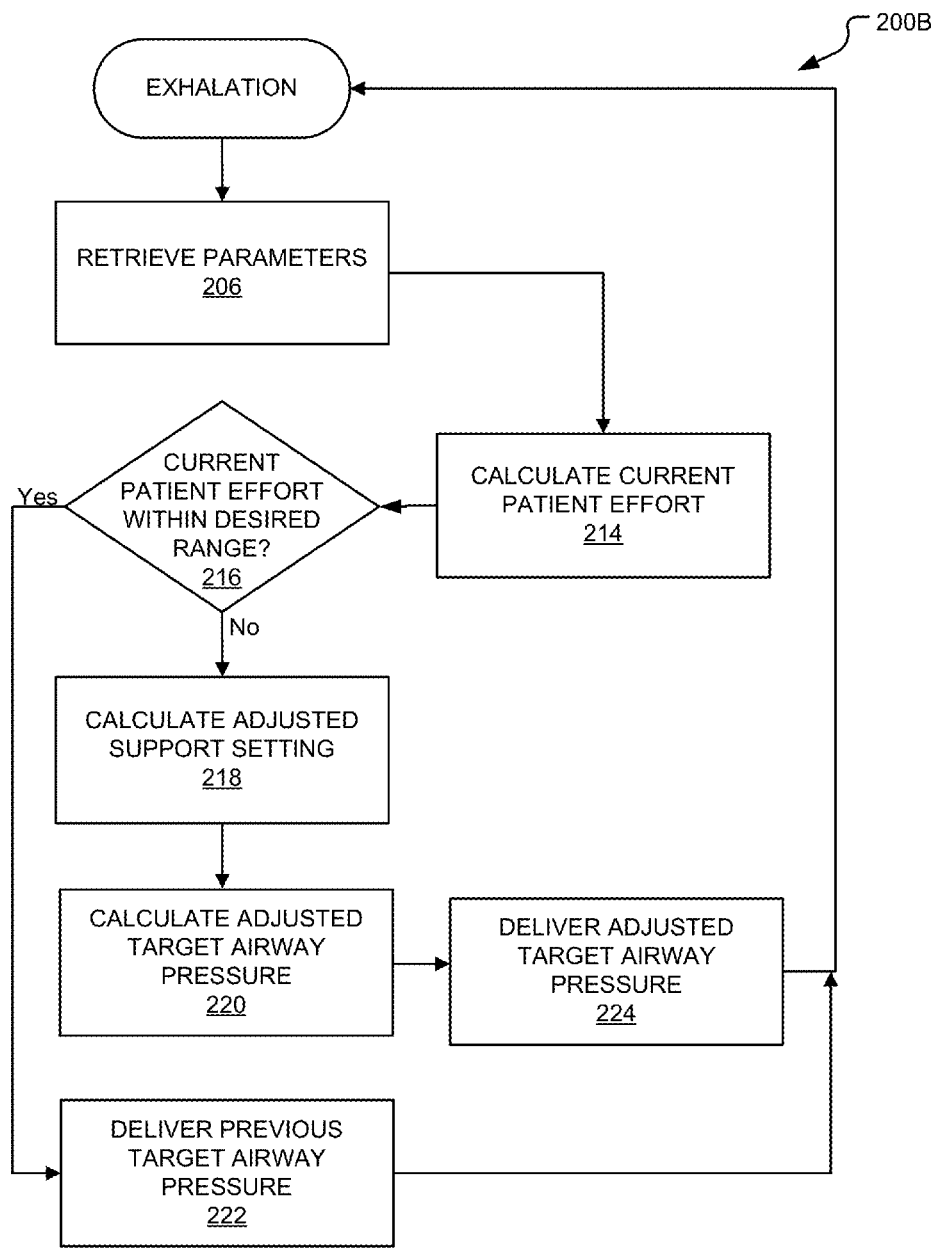
FIG. 2B illustrates an embodiment of a method for ventilating a patient on a ventilator during any breath after a first delivered breath in an optimized proportional assist breath type.

FIGS. 2A and 2B illustrate an embodiment of a method 200 for ventilating a patient with a ventilator that utilizes an OPA breath type. FIG. 2A illustrates an embodiment of method 200A for ventilating a patient with a ventilator for the first breath delivered during the OPA breath type. FIG. 2B illustrates and embodiment of method 200B for ventilating a patient with a ventilator for every breath delivered after the first breath during the OPA breath type.

The OPA breath type delivers a target airway pressure calculated based on a desired patient effort range. The desired patient effort range allows the ventilator to maintain a desired patient effort by adjusting a percent support setting. Further, the ventilator can maintain the patient effort to prevent muscle atrophy from non-use while at the same time preventing muscle fatigue from over-loading. Further, determining a desired patient effort range based on a desired treatment metric range in combination with the adjustment of ventilator parameter to maintain a desired treatment metric range can be utilized to improve the treatment of a patient on a ventilator.

As discussed above, method 200A illustrates the method for delivering the first breath during an OPA breath type. Accordingly, method 200A begins after the initiation of ventilation during an OPA breath type.

As illustrated, method 200A includes a retrieving operation 206. During the retrieving operation 206, the ventilator retrieves a desired patient effort range. The desired patient effort range represents a desired parameter from the patient effort profile over each breath. The desired patient effort may be a maximum, mean, root mean square (RMS), minimum or any other appropriate statistic of the a pressure waveform or patient muscle waveform during one breath or a window of multiple breaths. In one embodiment, the desired patient effort range (e.g., a desired peak muscle pressure) is retrieved from input or a selection made by the clinician. In this embodiment, the desired patient effort range does not change unless another range is entered by the clinician. In one embodiment, the desired patient effort ranges is from about 5 cm of H₂O to about 10 cm of H₂O. In other embodiments, the desired patient effort range is from about 4 cm H₂O to about 12 cm of H₂O. In some embodiments, the desired patient effort range is from about 6 cm H₂O to about 9 cm of H₂O. The desired patient effort range may not even be a range at all, but rather be a set value. Accordingly, the desired patient effort range may be 5 cm of H₂O, 6 cm of H₂O, 7 cm of H₂O, 7.5 cm of H₂O, 8 cm of H₂O, 9 cm of H₂O, or 10 cm of H₂O, for example. These lists are not meant to be limiting. Any suitable patient effort range to improve the health of the patient may be input by the operator and/or utilized by the ventilator.

Figure 3:
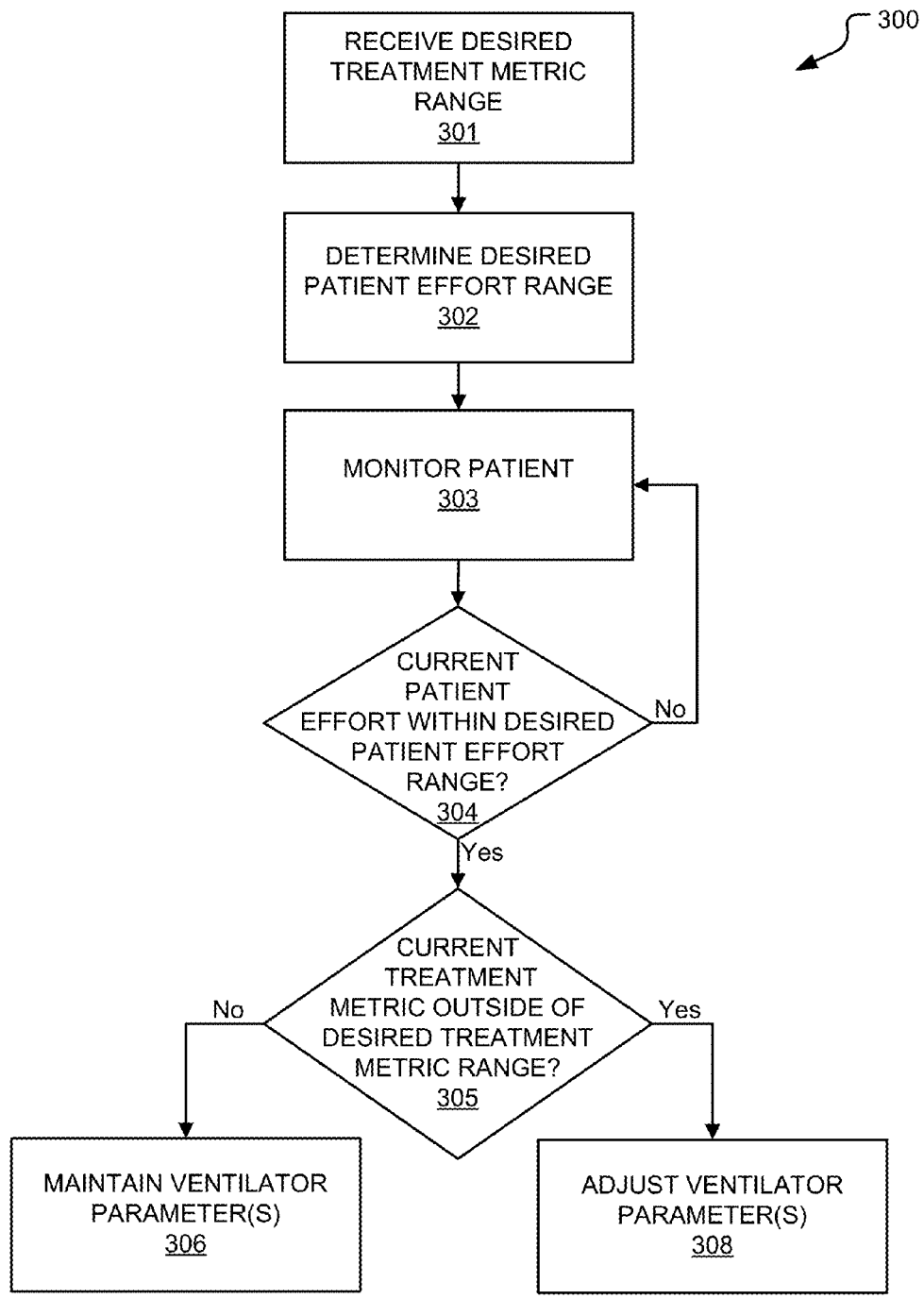
FIG. 3 illustrates an embodiment of method for ventilating a patient on a ventilator based on a desired treatment metric range during an optimized proportional assist breath type.

In another embodiment in which the ventilator is attempting to improve the treatment of the patient by determining the desired patient effort range based on a desired treatment metric range, the desired patient effort range is retrieved from a determination made by the ventilator during the retrieving operation 206. In this embodiment, the ventilator also retrieves during the retrieving operation 206 one or more one ventilator parameters from a ventilator determination about whether or not the current treatment metric is within the desired treatment range. An embodiment of a method for improving the treatment of the patient by utilizing a desired treatment metric range is illustrated in FIG. 3 and discussed in detail below.

Method 200A also includes an estimating operation 208. During the estimating operation 208 the ventilator estimates an initial percent support setting based on the desired patient effort range. The initial percent support setting as used herein is the percent support setting applied to at least the first breath delivered to the patient during execution of the OPA breath type. The initial percent support setting (k) is held constant over one breath. In one embodiment, the support module estimates the initial percent support setting by utilizing the follow equation based on the equation of motion:

$$\text{Patient Effort}(t) = (1.0 - k)[E_p \int Q_p dt + Q_p R_p].$$

The ventilator selects a Patient Effort (t) from the desired patient effort range and utilizes predetermined settings for the remaining parameters that cannot be determined since this is the first delivered breath. The predetermined settings may vary based on other parameters input by the clinician.

Next, method 200A includes a calculating first target airway pressure operation 210. During the calculating first target airway pressure operation 210, the ventilator calculates a first target airway pressure based on the initial percent support setting. The first target airway pressure is calculated for a point in the ventilation circuit that is proximal to the lung and would best assist the patient's inspiratory muscles to the degree as estimated in the initial percent support setting. The target airway pressure is calculated based on the equation of motion, such as by utilizing the following equation:

$$\text{Target Airway Pressure}(t) = k[E_p \int Q_p dt + Q_p R_p].$$

Method 200A also includes a first delivery operation 212. During the first delivery operation 212, the ventilator delivers a target airway pressure to a patient. The target airway pressure is delivered after an inspiratory trigger is detected. A patient trigger is calculated based on the at least one monitored parameter, such as inspiration flow. In some embodiments, sensors, such as flow sensors, may detect changes in patient parameters indicative of patient triggering. The target airway pressure delivered by the ventilator during the first delivery operation 212 is an initial target airway pressure calculated by the ventilator based on the initial percent support setting.

After the delivery of the target airway pressure by the ventilator during first delivery operation 212, the breath cycles to exhalation. As discussed above, method 200B illustrates the method for delivering any breath after the delivery of the first breath during an OPA breath type. Accordingly, method 200B begins during exhalation after any breath delivered during the OPA breath type.

As illustrated, method 200B also includes the retrieving operation 206. During the retrieving operation 206, the ventilator retrieves the current desired patient effort range. In some embodiments, the ventilator during the retrieve operation 206 further retrieves the desired treatment metric range, the current treatment metric, and one or ventilator parameters based on the desired treatment metric range. The desired patient effort range is changed by clinician input and/or a ventilator determination. For example, the clinician may change the desired patient effort range from 5 cm of $H_2O$ to 10 cm of $H_2O$ to a range of 7 cm of $H_2O$ to 9 cm of $H_2O$. In another example, the ventilator determines a patient effort range based on an input desired treatment metric range from an operator. In another embodiment, the clinician enters a new desired treatment metric range, such as a new RSBI setting range, which may be retrieved by the ventilator during the retrieving operation 206. Accordingly, the ventilator during retrieving operation 206 continuously retrieves the currently desired patient effort range and/or desired treatment metric range for the OPA breath type.

Further, method 200B includes a calculating current patient effort operation 214. During the calculating current patient effort operation 214, the ventilator calculates the current patient effort. The current patient effort or actual patient effort as used herein represents a time profile that depicts the amount of effort exerted by the patient during the last delivered breath. The current patient effort is calculated every control cycle based on the equation of motion and estimated patient parameters. The ventilator estimates patient parameters based on the measurements directly or indirectly related to monitored patient parameters. In some embodiments, the estimated patient parameters include lung compliance (inverse of elastance) and/or lung/airway resistance. In further embodiments, the estimated lung compliance, lung elastance and/or lung/airway resistance are estimated based on monitored flow and/or the equation of motion. The estimated patient parameters may be estimated by any processor found in the ventilator.

Next, method 200 further includes a decision operation 216. The decision operation 216 determines if the current patient effort is within the desired patient effort range. The ventilator during decision operation 216 utilizes the most updated desired patient effort as retrieved by the ventilator during the retrieving operation 206. If the ventilator during the decision operation 216 determines that the current patient effort is within the desired patient effort range, then the ventilator selects to perform delivery operation 222. If the ventilator during the decision operation 216 determines that the current patient effort is not within the desired patient effort range, then the ventilator selects to perform calculating adjusted percent support setting operation 218.

Method 200 includes a calculating adjusted percent support setting operation 218. During the calculating adjusted percent support setting operation 218, the ventilator calculates or determines an adjusted percent support setting. In one embodiment, when the current patient effort is greater than the desired patient effort range, the ventilator increases the percent support setting during the calculating adjusted percent support setting operation 218. In an alternative embodiment, when the current patient effort is below the desired patient ranges, the ventilator decreases the percent support setting during the calculating adjusted percent support setting operation 218. In one embodiment, the ventilator adjusts the percent support setting by utilizing an optimization algorithm during the calculating adjusted percent support setting operation 218. Example optimization algorithms are listed below in the Example section.

Next, method 200 includes a calculate an adjusted target airway pressure operation 220. During the calculate operation 220, the ventilator calculates an adjusted target airway pressure based on the received adjusted percent support setting. The adjusted target pressure is calculated every control cycle using the adjusted percent support setting by the ventilator during the calculate an adjusted target airway pressure operation 220. The adjusted support setting (k) is held constant over one breath. The adjusted target airway pressure is calculated for a point in the ventilation circuit that is proximal to the lung and would best assist the patient's inspiratory muscles to the degree as estimated in the initial percent support setting. The adjusted target airway pressure as used herein is the most recently calculated target airway pressure after the calculation of the initial target airway pressure. Accordingly, the adjusted target airway pressure may change periodically based on changes in at least one of the percent support setting, current patient effort, and/or the desired patient effort range. The adjusted support setting (k) is held constant over one breath. The adjusted target pressure is calculated every control cycle based on the equation of motion, such as by utilizing the following equation:

$$\text{Target Airway Pressure}(t) = k[E_p \int Q_p dt + Q_p R_p]$$

Next, method 200 includes an adjusted delivery operation 224. During the delivery operation 224, the ventilator delivers the adjusted target airway pressure to a patient. The ventilator delivers the adjusted target airway pressure to the patient after the detection of a patient initiated inspiratory trigger.

Further, method 200 includes a previous delivery operation 222. During the delivery operation 222, the ventilator delivers the previously delivered target airway pressure to the patient based on the previous percent support setting. The ventilator delivers the previously delivered airway pressure to the patient after the detection of a patient initiated inspiratory trigger. The previously delivered target airway pressure as used herein is the target airway pressure that was delivered during the last preceding breath. Accordingly, in some embodiments, the previously delivered target airway pressure is the initial target airway pressure. The previously delivered target airway pressure is the initial target airway pressure if the initial percent support setting caused the patient to exert a patient effort within the desired patient effort range. In another embodiment, the previously delivered target airway pressure is a previously adjusted target airway pressure. The previously delivered target airway pressure is a previously adjusted target airway pressure if the previously adjusted percent support setting caused the patient to exert a patient effort within the desired patient effort range.

In some embodiments, method 200 includes a display operation. The ventilator during the display operation displays any suitable information for display on a ventilator. In one embodiment, the display operation displays at least one of the current patient effort, the desired patient effort range, the desired treatment metric range, the current treatment metric, the RSBI, the $SpO_2$, the $P_{100}$, the tidal volume, the $VCO_2$, the respiratory rate, the spontaneous I:E volume, the minute volume, the initial percent support setting, and the adjusted percent support setting.

FIG. 3 illustrates an embodiment of a method 300 for ventilating a patient with a ventilator based on a desired treatment metric range during an OPA breath type. In embodiments, method 300 is performed for every breath or in a predetermined number of breaths.

As illustrated, method 300 includes a receiving operation 301. During the receiving operation 301, the ventilator receives a desired treatment metric range. The desired treatment metric range is received from input or a selection by the clinician. A treatment metric is a ventilator parameter that is indicative of how well a patient treatment is going. In some embodiments, the treatment metric includes RSBI, $SpO_2$, $P_{100}$, oxygen index, $ETCO_2$, tidal volume, $VCO_2$, respiratory rate, spontaneous I:E ratio, and a minute volume. In some embodiments, the treatment metric range includes a trended or weighted combination of at least one of RSBI, $SpO_2$, $P_{100}$, oxygen index, $ETCO_2$, tidal volume, $VCO_2$, respiratory rate, spontaneous I:E ratio, and a minute volume. The desired treatment metric range is a range of a ventilator parameter that improves the treatment of the patient. For example, if the treatment metric is RSBI, the desired treatment metric may be a range of an RSBI of less than 105, which helps to decrease the amount of time a ventilator takes to wean a patient from ventilation. In another embodiment, the desired treatment range is represented by a solitary values, such as and RSBI of 100.

Next, method 300 includes a determining operation 302. During the determining operation 302, the ventilator determines the desire patent effort range based on the received desired treatment metric range. The determined desired patient effort range should help the patient achieve a current treatment metric within the desired treatment metric range. The current treatment metric as used herein represents the treatment metric as measured or determined by the ventilator for the patient within the last computational cycle or for the last delivered breath depending upon the treatment metric utilized. In some embodiments, the treatment metric (whether current or desired) is derived from the calculated profiles over numerous breaths. In some embodiments, the treatment metric is the maximum, mean, root mean square (RMS), or any other appropriate statistic of the waveform during one window or a window of multiple breaths.

As illustrated, method 300 includes a monitoring operation 303. During the monitoring operation 303, the ventilator monitors patient parameters. In some embodiments, the patient parameters include the current treatment metric and the current patient effort. The monitoring operation 303 may be performed by sensors and data acquisition subsystems. The sensors may include any suitable sensing device as known by a person of skill in the art for a ventilator. In some embodiments, the sensors are located in the pneumatic system, the breathing circuit, and/or on the patient. In some embodiments, the ventilator during the monitoring operation 303 monitors patient parameters every computational cycle (e.g., 2 milliseconds, 5 milliseconds, 10 milliseconds, etc.) and/or during the delivery of the control pressure. In other embodiments, the trend of the monitored patient parameters are determined and monitored.

Next, method 300 includes a first decision operation 304. The ventilator during first decision operation 304 determines if current patient effort is within the desired patient effort range for at least two consecutive breaths. The ventilator determines if the current patient effort is within the desired patient effort range based on the monitored parameters and/or the received ventilator parameters. If the ventilator during the decision operation 304 determines that the current patient effort is within the desired patient effort range for at least two consecutive breaths, then the ventilator selects to perform second decision operation 305. If the ventilator during the first decision operation 304 determines that the current patient effort is not within the desired patient effort range for at least two consecutive breaths, then the ventilator selects to perform monitoring operation 303.

Next, method 300 includes a second decision operation 305. The ventilator during second decision operation 305 determines if the current treatment metric is outside of the desired treatment metric range. The ventilator determines if the current treatment metric is outside of the desired treatment metric range based on the monitored parameters and/or the received ventilator parameters. If the ventilator during the second decision operation 305 determines that the current treatment metric is not outside of the desired treatment metric range, then the ventilator selects to perform maintaining operation 306. If the ventilator during the decision operation 304 determines that the current treatment metric is outside of the desired treatment metric range, then the ventilator selects to perform adjusting operation 308.

Method 300 includes a maintaining operation 306. During the maintain operation 306, the ventilator maintains the current one or more ventilator parameters. Accordingly, the ventilator utilizes the one or more ventilator parameters as was utilized during the previous breath and/or control cycle. If there was no previous breath and/or control cycle, the ventilator during maintaining operation 306 utilizes predetermined ventilator parameters as set by the ventilator or as set by the operator. In one embodiment, the ventilator parameters include at least one of an oxygen percentage, a rise time, a trigger sensitivity, a peak flow rate, a peak inspiratory pressure, a tidal volume, and a PEEP.

Method 300 also includes an adjusting operation 308. During the adjusting operation 308, the ventilator adjusts the ventilator parameters based on the determination that the current treatment metric is not within the desired treatment metric range. The ventilator adjusts the ventilator parameters by utilizing algorithms and optimization programming techniques to provide advisory input and/or automatic adjustments to ventilation parameters and/or a timed changes in ventilation modality (patient-triggered or ventilator-driven breath delivery) to increase the efficiency and confidence in the predictive nature of the treatment metric. In other words, the ventilator during adjusting operation 308 adjusts the ventilator parameters in an attempt to make the next measured current treatment metric within the desired treatment metric range.

In one embodiment, the treatment algorithm and/or optimization programming incorporates an internal model of the patient respiratory system in interaction with the ventilator to address the relevant interactive dynamics between the patient and the ventilator as well as model and predict changes in patient's respiratory behavior and therapeutic outcome in response to the ongoing treatment protocol delivered by the ventilator. The control system design of the treatment module is envisioned to optimize convergence of the control output or desired patient effort. In some embodiments, the internal model for the treatment algorithm and/or optimization programming incorporates mechanisms for estimating system parameters (respiratory resistance, compliance, and etc.). Additionally, the treatment algorithm and/or the optimization programming may include features to estimate, model, or predict dynamics related to the functioning and interrelationships between inputs (e.g., percent support, $SpO_2$, oxygen mix, and etc.) and output (generated patient effort over time). In further embodiments, the treatment algorithm includes mechanisms to estimate physiologic-based and/or hardware-based dynamics (transients, delays, and etc.). For instance, an example treatment algorithm is listed below in the Example section.

The ventilator retrieves the desired patient effort range and the one or more ventilator parameters as determined by the ventilator during the maintaining operation 306 and the adjusting operation 308 during retrieving operation 206 for utilization in method 200. Accordingly, the ventilator during the retrieving operation 206 may retrieve a determined desired patient effort range and an adjusted one or more ventilator parameters or may retrieve the previously retrieved one or more ventilator parameters for use in method 200.

In some embodiments, a microprocessor-based ventilator that accesses a computer-readable medium having computer-executable instructions for performing the method of ventilating a patient with a medical ventilator is disclosed. This method includes repeatedly performing the steps disclosed in method 200 and/or method 300 above and/or as illustrated in FIGS. 2A, 2B, and/or 3.

In some embodiments, the ventilator system includes: means for retrieving a desired patient effort range; means for estimating an initial percent support setting based on the desired patient effort range; means for calculating a target airway pressure based at least on the initial percent support setting; and means for delivering the target airway pressure to a patient. In some embodiments, the ventilator system further includes: means for calculating current patient effort; means for determining if the current patient effort is above the desired patient effort range; and means for calculating an adjusted percent support setting that is greater than the initial percent support setting. In some embodiments, the ventilator system further includes: means for calculating current patient effort; means for determining if the current patient effort is below the desired patient effort range; and means for repeatedly calculating an adjusted percent support setting that is less than the initial percent support setting.

EXAMPLES

The examples listed below are exemplary only and not meant to be limiting of the disclosure.

Example 1

Example 1 illustrates an embodiment of a pseudo code for the systems and methods of the disclosure. The control objective is to maintain a defined metric of patient's respiratory effort (peak inspiratory muscle pressure (Pmus)) within a desired range by automatic adjustment of the "Percent Support Setting" parameter in an Optimized Proportional Assist Ventilation. The pseudo code illustrated below utilizes an algorithm that incorporates the following aspects:

The "Percent Support Setting" parameter is constrained between 0 and 100%.
The minimum increment/decrement for "Percent Support Setting"=1.0%
The "Percent Support Setting" parameter is adjusted every N breaths.
The "Desired Range" (Upper Bound=uBound, Lower Bound=1Bound) is given.
The desired bounds are constrained to lie between 0 and a feasible maximum range (with consideration of disease state).
The mid-point inside the desired range is the optimum value
The average of Peak Pmus over N breaths (AveragePmus) is the metric of choice Sample Algorithm:
The example implementation is envisioned to be done in two stages: (1) bring the measured Peak Pmus within the Desired Range, and (2) optimize measured Peak Pmus to the optimum value.

The pseudo code embodiment utilizing the algorithm described above is listed below (different sections of the pseudo code are divided by asterisks):

Optimum outcome parameter ranges: RSIB <105 ((breath/minute)/liter), 92%<$SpO_2$<99%, 38 mmHg<$etCO_2$<46 mmHg.

```
For every breath number i:
// increment breath count, and decide if it is time for adjustment
    MakeAdjustment (i)=false;
    Inc BreathCount;
//Check if it is time for the next adjustment, i.e., the window of N number of breaths have
passed;
  check if the total number of breaths counted is a multiple of the selected window (N).
If (MOD(BreathCount, N)=0)
MakeAdjustment(i)= true;
************************************************************
// Determine the operating zone.
    If ((AveragePmus)> uBound)
        Direction (i)=1
    Else
        If ((AveragePmus)< lBound)
        Direction(i)=-1
        Else
        Direction(i)=0
Else
    Skip Adjustment
************************************************************************
***
//Make adjustment algorithm
If (MakeAdjustment(i)= true)
    If (Direction(i)=0); Optimization Stage (Direction=0)
        Run Determine Optimized Percent Support;(algorithm below)
    Else; Bring-In Stage (Direction=1 or -1)
        If (Measured Metric>uBound)
            ControlError=Measured Metric-uBound;
        Else
            ControlError=Measured Metric-lBound;
        If (ABS (ControlError)>(uBound-lBound)) ; ABS( )=absolute value function
            controllerGain(i) =0.5
        Else
            controllerGain(i)=0.2
        If (Direction(i)≠Direction(i-1)); zero-crossing is detected
            controllerGain(i)= controllerGain(i-1)/2.0;
        New PercentSupportSetting=Previous PercentSupportSetting+
controllerGain(i)* ControlError;
*************************************************************************
**
// Determine Optimized Percent Support Setting Algorithm
    OptError=(uBound+lBound)*0.5- Measured Metric;
    Use Gradient Descent optimization method to minimize (ABS(OptError)); Broadly
speaking, increase/decrease PercentSupportSetting by 1 single point (minimum allowable
change) to determine the value that would minimize the magnitude of OptError.
```

Example 2

Example 2 illustrates an embodiment of a pseudo code for the systems and methods of the disclosure. The control objective is to optimize the treatment outcome based on a defined metric of weighted outcome results. The optimization is achieved by automatic controlling and adjusting ventilator parameters. Patient's respiratory effort (peak inspiratory muscle pressure) is maintained within a desired range by automatic adjustment of the "Percent Support Setting" parameter in Optimized Proportional Assist Ventilation.

The pseudo code illustrated below utilizes an algorithm that incorporates the following aspects:
  Outcome parameters include: RSBI (Breath Rate/Tidal Volume; weaning index), $SpO_2$ (patient's blood Oxygen saturation), and $etCO_2$ (end tidal $CO_2$).
  Ventilator settings allowed for automatic adjustment: Percent Support Setting (PAV), $O_2$%, PEEP.
  The "Percent Support Setting" parameter is constrained between 0 and 100%.
  $O_2$% is constrained between 21% and 100%.
  PEEP is constrained between 0 cmH2O and 25 cmH2O.
  The minimum increment/decrement for "Percent Support Setting"=1.0%
  The "Percent Support Setting" parameter is adjusted every N breaths.
  The "Desired Range" (Upper Bound=uBound, Lower Bound=lBound) of patient effort (Pmus) is given.
  The desired Pmus bounds are constrained to lie between 0 and a feasible maximum range (with consideration of disease state).
  The average of Peak Pmus over N breaths (AveragePmus) is the metric of choice for achieving the desired range.
Sample Algorithm:
The pseudo code embodiment utilizing the algorithm described above is listed below:
The example implementation is envisioned to be done in two stages:
  (1) Stage I: Bring the measured Peak Pmus within the Desired Range by adjusting the Percent Support Setting, and;
  (2) Stage II: While maintaining the Pmus within the desired range (by keeping the Percent Support Setting at the level determined in stage 1 and adjusting it if needed), adjust other ventilator parameters allowed to optimize the treatment outcome or treatment metric.

(3) Use the following Cost Function (C) for Stage II optimization:
Optimization Goal: {Minimize C};
C=α*WeaningMetric+β*OxygenationMetric+ Ω*VentilationMetric;
A, β, and Ω are relative weighting coefficients (range=0.00-1.00).
WeaningMetric=(measured RSBI-105);
OxygenationMetric=
(93-measured $SpO_2$) if measured $SpO_2$<93
0 if measured $SpO_2$>92
VentilationMetric=
(40-measured $etCO_2$) if measured $etCO_2$<40 mmHg
(measured $etCO_2$-45) if measured $etCO_2$>46 mmHg
0 if 39<measured $etCO_2$<46

Stage 1 (PAV Percent Support Setting Adjustment): see the Adjustment part of the Example 1 above for algorithms to bring in and maintain peak Pmus within the desired range.

Stage 2 (Outcome Optimization):
Maintain the peak Pmus within the desired range (by keeping the Percent Support Setting at the level determined in stage 1 and adjusting it if needed).
Use appropriate Reinforcement Learning and Dynamic Programming algorithms (for example, Gradient Descent) for multiple input parameters to optimize the weighted cost function C by programmed adjustments to PEEP and $O_2$% within their respective allowable ranges.
Provide progress reports (statistics, plots, etc.) as appropriate for monitoring purposes.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A ventilator system comprising:
a pressure generating system, wherein the pressure generating system generates a flow of breathing gas;
a ventilation tubing system including a patient interface for connecting the pressure generating system to a patient;
one or more sensors operatively coupled to at least one of the pressure generating system, the patient, and the ventilation tubing system, wherein the one or more sensors generate output indicative of an inspiration flow;
a support module that receives an initial percent support setting and a desired patient effort range, wherein the support module calculates at least one adjusted percent support setting based at least on determining that a current patient effort falls outside of the desired patient effort range, wherein the at least one adjusted percent support setting is calculated to cause the current patient effort to fall within the desired patient effort range when utilized to calculate an adjusted target airway pressure for delivery to the patient; and
an optimized proportional assist (OPA) module, the OPA module calculates an initial target airway pressure based at least on the initial percent support setting, calculates at least one adjusted target airway pressure based at least on the at least one adjusted percent support setting, and utilizes the output indicative of the inspiration flow to determine a patient trigger for delivery of a breath to the patient,
wherein the pressure generating system delivers the initial target airway pressure to the patient in response to receiving the initial target airway pressure and delivers the adjusted target airway pressure to the patient in response to receiving the adjusted target airway pressure affecting patient effort.

2. The ventilator system of claim 1, further comprising:
a treatment module, the treatment module determines the desired patient effort range based on a desired treatment metric range received from operator input and adjusts at least one ventilator parameter upon determining that a current treatment metric is not within the desired treatment metric range while the current patient effort is within the desired patient effort range for at least two consecutive breaths.

3. The ventilator system of claim 2, wherein the at least one ventilator parameter is at least one of oxygen percentage, rise time, trigger sensitivity, peak flow rate, peak inspiratory pressure, tidal volume, and PEEP.

4. The ventilator system of claim 2, further comprising a display that displays at least one of the current patient effort, the desired patient effort range, the desired treatment metric range, a current treatment metric range, a RSBI, a $SpO_2$, a $P_{100}$, a tidal volume, a $VCO_2$, a respiratory rate, a spontaneous I:E volume, a minute volume, the initial percent support setting, and the adjust percent support setting.

5. A ventilator system, comprising:
means for retrieving a desired patient effort range;
means for estimating an initial percent support setting based on the desired patient effort range;
means for calculating a current patient effort;
means for determining that the current patient effort is outside of the desired patient effort range;
means for calculating an adjusted percent support setting based on determining that the current patient effort is outside of the desired patient effort range, wherein the adjusted percent support setting is calculated to cause the current patient effort to fall within the desired patient effort range when utilized to calculate an adjusted target airway pressure for delivery to a patient;

means for calculating a target airway pressure based at least on the adjusted percent support setting; and means for delivering the target airway pressure to the patient to affect patient effort.

6. The ventilator system of claim 5, further comprising:

means for determining that the current patient effort is within the desired patient effort range; and means for delivering a previously delivered target airway pressure to the patient based on the means for determining that the current patient effort is within the desired patient effort range, wherein the means for delivering the target airway pressure to the patient is the same as the means for delivering the previously delivered target airway pressure.

7. The ventilator system of claim 5, further comprising:

means for receiving a desired treatment metric range from an operator;

means for determining that a current treatment metric is not within the desired treatment metric range; and means for adjusting at least one ventilator parameter until the current treatment metric is within the desired treatment metric range, wherein a means for determining the desired patient effort range determines the desired patient effort range based on the desired treatment metric range.

8. The ventilator system of claim 7, wherein the at least one ventilator parameter is at least one of oxygen percentage, rise time, trigger sensitivity, peak flow rate, peak inspiratory pressure, tidal volume, and PEEP.

9. The ventilator system of claim 7, wherein the desired treatment metric range is at least one of a trend and a weighted combination of at least one of RSBI, $SpO_2$, $P_{100}$, Oxygen index, $ETCO_2$, tidal volume, $VCO_2$, respiratory rate, spontaneous I:E ratio, and a minute volume.

10. The ventilator system of claim 7, wherein the desired treatment metric range is a range of at least one of RSBI, $SpO_2$, $P_{100}$, Oxygen index, $ETCO_2$, tidal volume, $VCO_2$, respiratory rate, spontaneous I:E ratio, and a minute volume.

11. The ventilator system of claim 5, further comprising:

means for receiving a desired treatment metric range from an operator, wherein a means for determining the desired patient effort range determines the desired patient effort range based on the desired treatment metric range.

12. The ventilator system of claim 5, wherein the target airway pressure is calculated utilizing a following equation:

$$\text{Target Pressure}(t) = k[E_p \int Q_p dt + Q_p R_p]$$

wherein Target Pressure (t) is an amount of pressure provided by the ventilator at time t, wherein k is a percent support setting, wherein $E_p$ is a respiratory elastance of the patient, wherein $Q_p$ is an instantaneous flow inhaled by the patient, and wherein $R_p$ is a respiratory resistance of the patient.

13. The ventilator system of claim 5, wherein the desired patient effort range is received from at least one of an operator via operator selection from a group of desired patient effort ranges, the operator via an input of a desired patient effort parameter, the ventilator system calculated based on at least one of an at least one monitored patient parameter and ventilator parameters, and the ventilator system via a selection from a group of predetermined patient efforts ranges based on at least one of the at least one monitored patient parameter and the ventilator parameters.

14. The ventilator system of claim 5, wherein the desired patient effort range is from about 5 cm of $H_2O$ to about 10 cm of $H_2O$.

* * * * *